US011833227B2

(12) United States Patent
Echols

(10) Patent No.: US 11,833,227 B2
(45) Date of Patent: Dec. 5, 2023

(54) METHODS FOR PRESERVING A SUBJECT AND USING IMAGING CONTRAST AGENTS

(71) Applicant: SICreations, LLC, Salt Lake City, UT (US)

(72) Inventor: Michael Scott Echols, Salt Lake City, UT (US)

(73) Assignee: SICREATIONS, LLC, Salt Lake City, UT (US)

( * ) Notice: Subject to any disclaimer, the term of this patent is extended or adjusted under 35 U.S.C. 154(b) by 345 days.

(21) Appl. No.: 16/888,114

(22) Filed: May 29, 2020

(65) Prior Publication Data
US 2020/0376143 A1 Dec. 3, 2020

Related U.S. Application Data

(60) Provisional application No. 62/853,837, filed on May 29, 2019.

(51) Int. Cl.
| | | |
|---|---|---|
| *A61B 5/055* | (2006.01) | |
| *A61K 49/04* | (2006.01) | |
| *A61K 49/06* | (2006.01) | |
| *A01N 1/00* | (2006.01) | |
| *A61K 49/22* | (2006.01) | |

(52) U.S. Cl.
CPC ............ *A61K 49/0438* (2013.01); *A01N 1/00* (2013.01); *A61K 49/04* (2013.01); *A61K 49/06* (2013.01); *A61K 49/22* (2013.01)

(58) Field of Classification Search
CPC .... A61K 49/0438; A61K 49/04; A61K 49/06; A61K 49/22; A01N 1/00
See application file for complete search history.

(56) References Cited

U.S. PATENT DOCUMENTS

| | | |
|---|---|---|
| 6,246,901 B1 | 6/2001 | Benaron |
| 2004/0052728 A1 | 3/2004 | Eriksen et al. |
| 2004/0241093 A1 | 12/2004 | Lauenstein et al. |
| 2008/0003561 A1 | 1/2008 | Woods et al. |
| 2010/0166664 A1 | 7/2010 | Butts et al. |
| 2011/0027275 A1 | 2/2011 | Ferrara et al. |
| 2011/0243847 A1 | 10/2011 | Wiebelitz |
| 2012/0297593 A1* | 11/2012 | Berry ................ A01N 1/00 27/22.2 |
| 2013/0224724 A1* | 8/2013 | Tousimis ............. A01N 1/00 435/284.1 |
| 2015/0359475 A1 | 12/2015 | Bennett et al. |
| 2016/0030601 A1 | 2/2016 | Echols |
| 2019/0059361 A1* | 2/2019 | McIntyre ............. A01N 1/00 |

FOREIGN PATENT DOCUMENTS

| | | |
|---|---|---|
| WO | 2019/099334 A9 | 5/2019 |
| WO | 2020/198534 A1 | 10/2020 |

OTHER PUBLICATIONS

Gi et al. (ASA abstracts A3274, Oct. 14, 2013).*
Balta et al. (J. Forensic Radiol. Imag. 2017, 11, 40-46).*
International Search Report and Written Opinion of the International Searching Authority for application No. PCT/US2020/25072, dated Jun. 18, 2020.
International Search Report and Written Opinion of the International Searching Authority for application No. PCT/US2020/35346, dated Aug. 28, 2020.
Grabherr et al. "Postmortem Angiography: Review of Former and Current Methods", American Journal of Roentgenology, vol. 188, Mar. 2007, pp. 832-838.
Johnson et al. "Correlation of Optical and MR Microscopy Images for Histology", International Society for Magnetic Resonance in Medicine, ISMRM, 1994, p. 718.
Schmit et al. "Safe ex vivo coronary angiography with isosmotic contrast agent", The Journal of Thoracic and Cardiovascular Surgery, vol. 112, No. 2, 1996, pp. 306-309.
Vrselja et al. "Restoration of brain circulation and cellular functions hours post-mortem", Nature, vol. 568, Apr. 18, 2019, pp. 336-343.
Extended European search report from European Patent Application No. 20812864.5, dated Jan. 5, 2023, 11 pages.

* cited by examiner

*Primary Examiner* — Michael G. Hartley
*Assistant Examiner* — Melissa J Perreira
(74) *Attorney, Agent, or Firm* — STEPTOE & JOHNSON LLP; Carl B. Wischhusen

(57) ABSTRACT

A method that may be used in the imaging of tissues or subjects includes flushing a tissue or subject with a solution, preserving the tissue or subject, and then introducing an imaging contrast agent into the tissue or subject. After these actions, the tissue or subject may be imaged.

16 Claims, 16 Drawing Sheets

(11 of 16 Drawing Sheet(s) Filed in Color)

METHODS FOR PRESERVING A SUBJECT AND USING IMAGING CONTRAST AGENTS

CLAIM OF PRIORITY

This application claims priority from U.S. Provisional Application No. 62/853,837 filed on May 29, 2019, which is incorporated by reference in its entirety.

BACKGROUND

Embodiments of the present invention relate to the field of imaging and in particular to tissue preservation methods to be used with contrast agents for imaging and postmortem manipulation.

The field of imaging (or visualization) runs from simple observation of treated subjects to advanced imaging using X-ray based technology including Computed Tomography (CAT or CT scans), high resolution photography, ultrasound, thermography, and magnetic resonance imaging (MRI). In radiographic imaging studies, a relatively opaque white appearance corresponds to dense materials or substances, compared with a relatively darker appearance of less dense materials.

Tissue preservation techniques, primarily used in deceased or otherwise non-living organisms, are employed to extend the viability or functional use of a subject beyond its natural degradation period. The ability to combine tissue preservation with contrast agents allows for more extensive testing, imaging, dissection, surgical training, research, and other procedures of the subject beyond the natural degradation period thereby increasing use and potential to gain knowledge of the subject.

"Radiodensity" or "radiopacity" refers to the relative inability of electromagnetic radiation, particularly X-rays, to pass through a particular material. "Radiolucency" indicates greater transparency or "transradiancy" to X-ray photons. Materials that inhibit the passage of electromagnetic radiation are called "radiodense," while materials that allow radiation to pass more freely are referred to as "radiolucent."

Contrast agents may be used to highlight specific structures to improve visualization of living and deceased organisms and non-biologic subjects. Radiodensity is measured on a Hounsfield unit (HU) scale. The HU scale is considered standardized with radiodensity of air at standard temperature and pressure as −1000 HU and water as 0 HU (as examples). In the field of medicine, radiographic imaging has been revolutionized by radiodense contrast media, which can be passed through the bloodstream, the gastrointestinal tract, or into the cerebral spinal fluid. The radiodense contrast media may be utilized to highlight computed tomography (CT) scan or X-ray images, and provides the ability to generate highly accurate and detailed anatomic and physiologic images of the body in a noninvasive manner.

Magnetic resonance imaging (MRI) uses magnetic fields and radio waves to generate images. While both CT and MRI differentiate tissue density, MRI more accurately differentiates proton (mostly hydrogen) densities. MRI also differentiates between tissue relaxation relative to magnetization. Because hydrogen protons predominate in water, soft tissue generates more "signal" than bone with MRI. The larger the MRI magnet (measured in Teslas or "T"), the better the ability of the machine to distinguish between the biologic states of the atoms it is reading. This translates into better resolution of the final images. The magnet aligns the protons. Subsequently, the machine produces radiofrequency waves that vary the magnetic field and disrupts the protons' spins. The field is then turned off and the protons return to their normal spin ("reorient") producing a radio signal that is measured by the detector. These data are then converted into an image. During a T1-weighted image or MRI, protons reorient resulting in recovery of longitudinal magnetization. T1 images show water (like cerebrospinal fluid (CSF)) as dark and fat (like white matter) as white. T1 images are good at demonstrating anatomy. During a T2-weighted image or MRI, protons reorient resulting in decay of transverse magnetization. In T2 images water appears bright and fat appears dark. Because many diseases are associated with a change in water content, T2 images are better at showing pathology. Contrast agents such as those containing gadolinium based (best for T1 studies) and iron based (best for T2 studies) products can be used to enhance the MRI signal and subsequent images.

Ultrasound (or ultrasonography) provides real-time (immediate) information of a scan area and is readily available and typically lower cost than both CT and MRI. Ultrasound uses high frequency sound waves to delineate tissue structures. The ultrasound transducer converts electrical signals into ultrasound waves that are directed into a subject's tissues. The sound waves bounce off the subject's tissues and return to the transducer where the returned sound waves are converted back into electrical signals. A computer then converts the electrical signals into an image. Images represent the tissue's relative effect on the passing sound wave. Water-based tissues tend to be good transducers of sound waves while those with air, metal, bone, stones, and metal implants are poor transducers. Thus, dense (e.g., bone) and air-filled tissues tend to block the passage of ultrasound waves creating image voids or artifacts, which can be used to obscure or differentiate and identify tissues. Moreover, only a small area can be scanned at any given time. Contrast agents, including microbubbles, can be added to the bloodstream to enhance the ultrasound signal and resulting image.

High resolution photography may also be used to visualize structures of a subject. Newer camera technology products are capable of resolutions of 10 microns or less. This technology is likely to improve over time. Subjects may be photographed externally or microtome sliced and photographed at each slice level. The photographs may be compiled (much like a CT or MRI) to create stacks of images that can then be studied three dimensionally creating exceptional studies that accurately depict the 3D structures of the subject. Although the method described (microtomy) is destructive, it does allow for a detailed accounting of the subject. Contrast agents can be added systemically or at each level of the subject "slice" to highlight specific or multiple structures. Additionally, before and after images of the unaltered and contrast-stained slice may be studied via subtraction and other methods to visually enhance or highlight specific structures (with and without "stain").

Each of these modalities has some benefits. Conventionally, CT has advantages in terms of speed and resolution for visualizing the skeletal system, whereas MRI offers unparalleled soft-tissue contrast (e.g., grey and white matter in the brain). Ultrasound best provides information on soft tissue structures and flow (doppler ultrasound) and usually as a 2D image (although 3D/4D constructs are possible). Newer digital camera technology offers true color image capture at incredible detail.

There are different types of materials that can be used as a contrast agent. Iodine and barium compounds are used as a contrast agent because of their high X-ray absorption. Dimethyl sulfoxide (DMSO) and alcohol may be used as contrast agents. Heavy metals such as lead, mercury, cadmium, copper, and uranium may be used as contrast agents. Resins, such as methyl methacrylate-based compounds, may also be used as contrast agents. A resin fills a subject's vasculature and then polymerizes. After polymerization, the tissue can be dissolved, thin-sliced, or otherwise modified and a fragile construct forms that can be imaged. A drawback is that filling the vasculature with a resin takes a long time.

By using either exogenous or endogenous contrast agents, additional imaging and information of the body can be captured. For example, images of the vascular system (i.e., angiography) can be obtained via contrast-enhanced digital subtraction CT or time-of-flight MRI. The detailed morphological analysis of the vascular tree allows for assessing the basic anatomy, physiological conditions, and metabolic functions of the subject.

Several contrast agents are commonly used with MRI. Most contrast agents, such as gadolinium-based compounds, work by shortening the T1 relaxation time of protons which in turn enhances the signal. The contrast agents are typically used on live animals yet are also operative in non-living tissues and subjects. Most contrast agents are delivered via intravenous (IV) or intrathecal routes. Some contrast agents can be administered orally for gastrointestinal MRI studies. Gadolinium chelates are hydrophilic and do not cross the blood-brain barrier, thus, these compounds can be useful in visualizing tumors and other lesions that break down this barrier. The gadolinium essentially exits the vasculature defining the abnormal tissue. OMNISCAN® (gadodiamide, GE HealthCare) and PROHANCE® (gadoteridol, Bracco Imaging) are examples of available gadolinium-based MRI contrast agents. Prepared BRITEVU® (barium based, Scarlet Imaging, LLC, and detailed in US2016/0030601A1) solution is composed primarily of water (a source of hydrogen protons), and this contrast agent provides excellent MRI contrast for terminal studies. Additionally, gadolinium can be added to the BRITEVU® solution for additional MRI contrast. Other contrast agents, like iron-containing compounds, affect T2 relaxation for MRI studies. Other metal chelates are available that can target specific tissues or cells.

Several contrast agents can be used with ultrasound. By simply filling collapsed vessels with fluid, gel, and other semisolid compounds, ultrasound image contrast may be improved. Microbubble contrast agents include sulphur hexafluoride microbubbles (SONOVUE®, Bracco Imaging), octafluoropropane gas core with an albumin shell (OPTISON, GE Healthcare) and air within a lipid/galactose shell (LEVOVIST, Schering AG), and all serve to improve the image information content during an ultrasound study. Many of the microbubble products have been shown to be safe for use in live subjects. Fabrizio Calliada et al., Ultrasound Contrast Agents: Basic Principles, 27 Eur. J. Radiology, Suppl 2:S157-60 (May 1998). Water-based terminal contrast agents (such as BRITEVU®) that fill the vasculature can also improve ultrasound imaging.

Regarding photography, many contrast agents can be used to spot or systemically "stain" tissue to enhance certain structures. For example, fluorescein dye can be added to vascular-delivered (CT, MRI and ultrasound) contrast agents to better highlight the vascular system using standard (e.g., incandescent) and UV light. In another example, many iodine-based compounds stain different tissues a differential brown hue that be can be used to highlight specific structures. In another example, silver-based stains tend to impart a grey-blue to black hue to stained nervous tissue depending on the specific nerve type. All are examples of how tissue stains can be used to enhance photographic images.

Contrast imaging began as early as the 1920s with the use of barium swallows visualized with X-ray technology, and since then many forms of contrast agents have been developed and used in medicine, research, the arts, and other applications. Many types of contrast agents have been practiced on biologic (both live and dead) and non-biologic specimens.

Today, contrast-based studies are commonplace in clinical and research-based applications. In 2015, Beckett et al. reported "half of the approximately 76 million computed tomographic (CT) and 34 million magnetic resonance imaging (MRI) examinations performed each year include the use of intravenous contrast agents." Katrina R. Beckett et al., *Safe Use of Contrast Media: What the Radiologist Needs to Know*, 35 RadioGraphics 1738-1750 (October 2015).

Contrast agents work by enhancing subject matter visualization. For example, iodinated and other compounds (sodium, bismuth, potassium and lithium iodide, Lugol's iodine, clinical iodine-based compounds, barium-based products, gold nanoparticles, and others) increase the X-ray attenuation of tissues that take up (diffusible), or are in contact with (perfusible), the contrast agent. By increasing relative density, contrast agents help make the target tissue/subject more visible using X-ray technology such as CT scanning. MRI contrast agents work by shortening or increasing the T1 or T2 relaxation time of exposed tissues. Relative differences in the T1 relaxation time of water protons in different tissues primarily provides contrast seen in magnetic resonance (MR) images. Gadolinium-based contrast agents affect T1 relaxation time.

T2 relaxation times also affect MR images and can be altered by iron and other materials contained or used in contrast agents. As above, vascular and tissue filling agents and microbubble intravascular agents can improve ultrasound studies. Traditionally, contrast agents used with advanced imaging have been divided into diffusible and perfusible categories.

Diffusible contrast agents are those that diffuse across membranes. The subject to be imaged is often soaked in a solution containing a diffusible agent illustratively including Lugol's iodine. Some agents such as hexamethyldisilazane can be combined with drying agents, such as alcohols, to increase tissue contrast when viewed with X-rays. Diffusible agents diffuse at specific rates and often must be replenished until the subject is adequately contrast stained (as determined by advanced imaging). The subject can be living, dead, biologic, and non-biologic. The size of the subject is often the rate-limiting consideration as diffusible contrast agents can only diffuse small areas (often on the level of mm or cm in depth). As noted by Gignac et al., "specimens should be fixed thoroughly prior to staining and imaging." Paul M. Gignac et al., Diffusible Iodine-Based Contrast-Enhanced Computed Tomography (diceCT): An Emerging Tool for Rapid, High-Resolution, 3-D Imaging of Metazoan Soft Tissues, 228 J. Anat. 889-909 (June 2016). Fixation prior to contrast diffusion prevents degradation of the tissue while waiting for complete penetration of the diffusion agent. However, an entire diffusion process can take days or weeks to months. Furthermore, fixation protocols can distort tissue by cross-linking proteins, changing tissue water content, and other changes. These distortions may ultimately result in altered anatomy of the subject even if the subject is not physically handled or further manipulated.

Diffusible agents can contrast stain (or enhance) multiple tissue types present in a penetration zone, and allow for differential "staining." When viewed using advanced imaging, differential staining translates into varying degrees of contrast uptake. The end result is that tissues with different contrast amounts appear visually distinct from one another especially when viewed with advanced imaging (CT, MRI, etc.). The differential staining allows viewers to identify specific tissues, portions of tissues, and even different cells when using micro-imaging techniques as with some micro-CT and nano-CT studies.

Among the challenges of using diffusible agents is getting different tissue types (including down to cell level) to not only stain (take up contrast) differentially, but also evenly diffuse throughout the tissue being stained. Uneven distribution of the contrast stain tends to result in some areas (most often those in first contact with the agent) to overstain (which may be represented as excess radiodensity or T1/T2 relaxation on a CT scan or MRI, respectively). Likewise, those tissues furthest from the closest point of contact with the contrast stain may be understained (which may be represented as low radiodensity on CT or minimal effect on T1/T2 relaxation times).

One partial solution to uneven uptake of diffusible agents is to administer the diffusible agents via a route that more evenly exposes the test subject. An example of this is using diffusible agents like a perfusible product by injecting the stain into the vascular system. This process more evenly exposes the test subject. However, it does not address the overstaining issue as the tissues of first contact are still at risk of taking on too much contrast agent and artificially representing contrast stain uptake Perfusible (or perfusion-based) contrast agents are delivered into a system (such as the circulatory, respiratory or lymphatic system) and do not cross the barrier of the system (assuming there is no functional break in a membrane, etc.). Perfusible contrast agents can be applied to living, dead, biologic and non-biologic systems.

Examples of perfusible agents include barium swallows for gastrointestinal contrast studies and iodinated compounds delivered intravenously for arteriovenograms. Perfusion-based agents are generally rapidly administered and define the shape and course only of the system being perfused when viewed with various imaging modalities. Often, perfusible agents never leave the perfused system (unless a rupture is present) and are ultimately eliminated from the subject. Some perfusible agents replace the normal volume of fluid and are permanent, such as terminal vascular casting agents. Perfusible agents are commonly used for both CT and MRI contrast studies.

However, perfusible contrast agents may be used in other imaging modalities such as microbubbles and simple fluid volume loading used in ultrasound as described by Calliada et al.

Examples of CT-perfusible contrast agents include iohexol (OMNIPAQUE®, GE Healthcare); iopromide (ULTRAVIST®, Bayer Healthcare); iodixanol (VISIPAQUE®, GE Healthcare); ioxaglate (HEXABRIX®, Mallinckrodt Imaging); iothalamate (CYSTO-CONRAY® II, Mallinckrodt Imaging); iopamidol (ISOVUE®, Bracco Imaging); and diatrizoate (Renagrafin-76, Bracco Imaging). See Hrvoje Lusic and Mark W. Grinstaff, *X-Ray Computed Tomography Contrast Agents*, 113 Chem. Rev. 1313-1350 (March 2013). Lanthanide-based contrast agents are used primarily with MRI contrast imaging, but are sometimes also used with CT testing. Examples of lanthanide-based contrast agents used with CT and/or MRI testing include gadoversetamide (OPTIMARK®, Mallinckrodt Imaging), gadopentetate dimeglumine (MAGNEVIST®, Bayer Healthcare), gadobutrol (GADOVIST, Bayer Healthcare), gadobenate dimeglumine (MULTIHANCE®, Bracco Imaging), gadoterate meglumine (DOTAREM®, Guerbet), and gadoxetate disodium (EOVIST®, Bayer Healthcare). See Lusic and Grinstaff, supra. Terminal perfusible contrast agents (such as BRITEVU®) are often used to fill the internal structure of a system (respiratory, circulatory, etc.).

Other products have also been used as contrast agents to create special images (CT, MRI, ultrasound, etc.), see Lusic and Grinstaff, illustratively including gas bubbles, bismuth, silver, gold, iron, platinum, lead, rare-earth-based elements, nanoparticles, and entrapped, conjugated, labeled, coated, or otherwise connected monoclonal antibodies, tissue receptors (for example, gastrin, folic acid, vitamin D), lipoproteins (high density lipoproteins, low density lipoproteins, etc.), cell specific (kidney, liver, etc.), tantalum, and high-Z noble gases (Xenon, etc.).

While perfusible contrast agents define the intact system into which the contrast agent(s) is(are) perfused, perfusible contrast agents do not generally contrast stain other tissues. In some cases, components of the perfused subject may selectively take up the stain and store it temporarily to permanently. For example, liver cells may selectively take up components of a systemic stain which would then highlight the target organ (liver in this example) and less so the entire subject. Still, all the diverse tissues/components of the subject are not differentially stained.

X-ray technology generally defines five basic density types: air, fat, soft tissue, bone, and metal. While CT generates composite X-ray (3-dimensional) images, the same five basic density types are seen. Software modification can improve some subtle variations in tissue density. However, resolution and differentiation of different soft tissue types is generally poor with CT.

MRI uses a different set of tissue differentiation principles including magnetic characteristics of tissues, movement of fluids (such as blood), and spectroscopic effects related to molecular structure. In terms of biologic tissues, variations in soft tissue structure are better defined with MRI compared with CT. However, MRI is generally deficient at providing information on those tissues that are poor in hydrogen such as bone and many manufactured products (metal, plastic, etc.).

Photography offers tremendous variation in how a true image is 'seen' by the camera or transmitted to film or digitally. For example, filtering (ultra-violet (UV), thermal, infrared, etc.) can alter the appearance of the image (and can be further enhanced by the addition of secondary agents such as contrast, fluorescein, cooling, heating and other agents) as seen by the camera. Post-processing software can then further alter the image to highlight specific structures, colors, wavelengths, focus, and other image attributes.

The main advantages of CT, X-ray, and photography technology is that these modalities are generally more available, less costly, more rapidly acquire images, and produce more detailed images compared to MRI. The advantages of MRI are the lack of radiation exposure (also true with photography and ultrasound) and increased soft tissue resolution compared to CT. Ultrasound also lacks radiation exposure and provides for good soft tissue resolution (primarily) in one tissue plane with each pass of the transducer.

Tissue preservation centers on delaying the natural degradation of tissues of living and non-living subjects. Subjects may be preserved using many methods, including cryopreservation, chemical agents, and substituting fluids that mimic the natural state of the tissue. Preservation methods tend to be temporary and may last from days to years depending on the subject and preservation method. Subject fixation is a more permanent method of preservation and may keep tissues stable for months to centuries depending on the subject and fixation method. While fixation methods tend to be harsher, having greater potential to alter one or more aspects of the subject, all preservation methods have the potential to result in subject changes. Thus there is often a trade-off between the amount of subject alteration and the ability to stop or delay natural degradation for a time period long enough to complete post-mortem evaluation, manipulation, etc.

Preservation methods most commonly involve keeping the subject at specific temperatures, changing oxygen exposure, altering atmospheric pressure, altering storage humidity, heating the subject, increasing or decreasing subject osmolality, increasing or decreasing subject pH, immersing or perfusing with specific agents, or other methods designed to delay subject degradation. While lowering tissue temperature often slows tissue degradation in deceased biologic samples, increasing temperature may be employed to speed the rate of fixation with certain chemicals. Altering oxygen exposure and atmospheric pressure and exposing the subject to hyper and/or hypoosmolar and basic and/or acidic solutions are examples of means that slow biologic and some non-biologic tissue degradation. Immersion involves placing the subject in a solution, gas, or solid that cools, preserves, fixes, or otherwise protects the subject from degradation (via an outside-in approach). Immersive techniques are limited to the depth of penetration of the immersion substance and are generally restricted to smaller subjects depending on the method. Perfusion techniques usually involve passively or forcibly passing fluid, gas, or solid agents through a subject (often via a channel system such as blood vessels) to more diffusely protect the subject from degradation (via an inside-out approach). Perfusion methods tend to provide more complete subject preservation and/or fixation.

Various preservatives and fixatives can be used for different purposes. In general, the more permanent the preservation, the more tissue alteration that occurs. For example, aldehyde compounds (10-37% formalin, glutaraldehyde (a dialdehyde), etc.) tend to cross link proteins and stiffen tissue, an effect that becomes more exaggerated with higher concentrations and prolonged exposure. (Other aldehyde- or dialdehyde-based compounds include propionaldehyde, butyraldehyde, benzaldehyde, cinnarnaldehyde, vanillin, toluaidehyde, furfural, retinaldehyde, aiondialdehyde, glyoxal, succindialdehyde, and phthalaldehyde.) Precipitating or denaturing fixatives reduce solubility of protein molecules that may result in tissue shrinkage (ethanol and methanol) or swelling (acetic acid). Oxidizing agents, mercurials, and picrates are other fixative agents that preserve tissues in various ways, each with pros and cons. Sometimes different preservative/fixative agents are combined to act synergistically to delay degradation and reduce negative tissue altering effects. Non-formaldehyde-based and non-formaldehyde-containing compounds may be used as preservatives as relatively non-toxic alternatives to formaldehyde-based agents. Such compounds may include salt-based compounds and alcohol-based compounds. Salt-based compounds may include sodium chloride, potassium nitrate, sodium nitrate, potassium chloride, and calcium chloride, as well as other salt-based compounds disclosed above. Alcohol-based compounds may include isopropyl alcohol, ethanol, methanol, mannitol, sorbitol, inositol, glycerol, glycol (ethylene, propylene), erythritol, cetyl, geraniol, pentanol, butanol, xylitol, volemitol, menthol, and methyl or ethyl-based alcohols.

Human and animal cadavers are examples of subjects that often are preserved for use with teaching, surgical training, research, and more. The most common method of preservation is immediate cooling or freezing (post death) of the subject to create the most life-like subject. However, tissue degradation is rapid post-thaw, limiting the time of use of the previously frozen subject. Formalin (aldehyde-type) diffusion and/or perfusion is also common, however the use of formalin results in stiff and discolored tissue and uses potentially harmful chemicals. Thiel's solution and embalming method uses a combination of preservation methods (for synergistic action) with low levels of toxic compounds to create more life-like cadavers. However, the multi-step cadaver preparation process is considered expensive and technically difficult to complete. Saturated salt solutions offer a low-cost, less toxic method of preservation and can also be used in cadavers. Shogo Hayashi et al., *History and Future of Human Cadaver Preservation for Surgical Training: From Formalin to Saturated Salt Solution Method*, 90 Anat. Sci. Int. 1-7 (September 2015); Nicolás E. Ottone et al., *Walter Thiel's Embalming Method. Review of Solutions and Applications in Different Fields of Biomedical Research*, 34 Intl J. Morphol. 1442-1454 (December 2016); Shogo Hayashi et al., *Saturated Salt Solution Method: A Useful Cadaver Embalming for Surgical Skills Training*, 93 Medicine (v. 27) 1-10 (December 2014). Several other cadaver preparation methods, for example, the Graz, Dodge, modified Larssen, "Fix for Life," Genelyn preparations, etc., have been published and typically involve perfusion methods with variable outcomes relative to tissue color, flexibility, pliability, and susceptibility to degradation, such as that caused by fungal growth. Rebekah Jaung et al., *A Comparison of Embalming Fluids for Use in Surgical Workshops*, 24 Clin Anat. (v. 2) 155-161 (March 2011); Okan Bilge and Servet Celik, *Cadaver Embalming Fluid for Surgical Training Courses: Modified Larssen Solution*, 39 Surg. Radiol. Anat. 1263-1272 (November 2017); Michael W. van Emden et al., *Comparison of a Novel Cadaver Model (Fix for Life) With the Formalin-Fixed Cadaver and Manikin Model for Suitability and Realism in Airway Management Training*, 127 Anesth. Analg. 914-919 (October. 2018); Joy Y Balta et al., *Human Preservation Techniques in Anatomy: A 21st Century Medical Education Perspective*, 28 Clinical Anatomy 725-734 (June 2015).

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Figure 1:
FIG. 1 is an image of a human female cadaver tissue-stained interstitium with a contrast agent in accordance with embodiments of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The present invention is a method and system for preserving a subject and then introducing perfusible and/or diffusible contrast agents to the subject, thereby slowing or halting natural tissue degradation and allowing for prolonged post-mortem subject use for imaging and further study. Methods and compositions for perfusible and/or diffusible contrast agents are disclosed in co-pending U.S. application Ser. No. 16/831,688, which is incorporated by reference herein in its entirety. Inventive embodiments of the preservation process are followed by perfusion with perfusible and/or diffusible contrast agents and allow for multiple uses of subjects over a prolonged time that would otherwise not be possible. Embodiments of the disclosed invention allow for improved utilization of human and animal cadavers for imaging along with teaching, surgical training, research, forensic, histology, and other studies that rely upon the identification, manipulation, or other use of the subject.

One of several distinctions between embodiments of this invention and previously described methods relates to first flushing the subject's (whether whole, regionally, by organ, etc.) vascular system combined with preservation agents with or without the use of preparation and/or conditioning agents, which is subsequently followed by perfusion with a contrast agent, with or without diffusion, topical exposure, etc. The process described herein allows for preserved cadavers containing contrast agents to potentially be used multiple times for imaging studies, dissection, surgical training, forensics, histology, etc., without concern of immediate tissue degradation.

Previous studies describe the use of frozen-thawed, fresh, or recently deceased cadavers that were or were not perfusion- or diffusion-fixed, or otherwise preserved and then perfused or diffused with contrast agents. Seervathsa Boraiah et al., *Assessment of Vascularity of the Femoral Head Using Gadolinium (Gd-DTPA)-Enhanced Magnetic Resonance Imaging: A Cadaver Study*, J. Bone Joint Surg. Br. 131-137 (January 2009); Akira Shinaoka et al., *A Fresh Cadaver Study on Indocyanine Green Fluorescence Lymphography: A New Whole-Body Imaging Technique for Investigating the Superficial Lymphatics*, 141 Plast. Reconstr. Surg. 1161-1164 (May 2018); Thilo L. Schenck et al., *The Functional Anatomy of the Superficial Fat Compartments of the Face: A Detailed Imaging Study*, 141 Plast. Reconstr. Surg. 1351-1359 (June 2018); Daniel Paech et al., *Contrast-Enhanced Cadaver-Specific Computed Tomography in Gross Anatomy Teaching*, 28 Eur. Radiol. 2838-2844 (July 2018); Amrita Sarkar et al., *Continuous Flow Perfused Cadaver Model for Endovascular Training, Research, and Development*, 48 Ann. Vasc. Surg. 174-181 (November 2017); Silke Grabherr et al., *Postmortem CT Angiography Compared with Autopsy: A Forensic Multicenter Study*, 288 Radiology 270-276 (July 2018); Ruben P. A. van Eijk et al., *Novel Application of Postmortem CT Angiography for Evaluation of the Intracranial Vascular Anatomy in Cadaver Heads*, 205 Am. J. Roentgenology 1276-1280 (December 2015); Christine Chevallier et al., *Postmortem Computed Tomography Angiography vs. Conventional Autopsy: Advantages and Inconveniences of Each Method*, 127 Intl J. Legal Med. 981-989 (January 2013). However, these previous methods lack a technique to adequately flush out the vasculature in preparation for contrast agent administration, and instead rely on no preservation or the combination of preservation followed by contrast agent administration.

As recently as 2018, it has been known to first contrast perfuse cadavers followed by preservation in 99% ethanol. See Paech, supra. However, this method does not permit thorough flushing prior to instillation of contrast agents post-preservation. Moreover, a cryopreservation solution flush has been used prior to contrast perfusion in human and dog kidneys which were removed from their respective subjects, with the objective to replace the excised organs for allograft surgery. See Ralph J. Alfidi and Magnus O. Magnusson, *Arteriography During Perfusion Preservation of Kidneys*, 114 Am. J. Roentgenology 690-695 (April 1972). This and similarly described methods utilize preservation techniques designed to keep tissue viable for transplantation and not for use with terminal studies, and are therefore distinctly different from embodiments of the present invention. Embodiments of the present invention dramatically improve the distribution of preservatives and contrast agent throughout the tissues of a deceased subject.

Embodiments of the present invention use preservation techniques that are delivered intravenously in an effort to slow or halt the degradation of the deceased subject. Preservation techniques may include the full range from soft embalming (resulting in soft and more life-like subject appearance) through hard fix (resulting in stiff and more permanently preserved tissue) techniques. Preservation techniques may also include relatively non-toxic (or reduced toxicity) (saturated salt solutions, glycol-based chemicals, etc.) as well as toxic (formaldehyde, glutaraldehyde, etc.) compounds used in the fixation/preservation process. The preservation process most commonly involves accessing a major artery or vein via a catheter, trocar, tubing, etc. as a means to deliver one or more of the preservation actions. Adjacent or distal blood vessels may be cannulated, catheterized, cut, or otherwise exposed to allow drainage of fluids out and away from the subject. If used alone, enough of the preservation (embalming) fluid is used to flush out the vasculature so as to remove most of the intravascular blood product and/or lyse the cellular components of the blood to significantly reduce clots that would otherwise obstruct vascular flow. Additional actions that may be employed to preserve tissue may include lowering cadaver temperature, spraying with anti-microbial sprays, etc.

In a specific embodiment of the present invention, the cadaver is first prepared by removing and/or lysing (primarily red blood cells) the majority of the blood via intravenous and/or intra-arterial catheterization, cannulation, etc. to deliver flush solutions prior to using preservation chemicals. Additionally, removal of blood from the vascular system may only be a portion of the preservation operation, which may further include removing sugars, fats, proteins, infectious agents, toxins, etc., that normally accelerate microbial growth, increase enzymatic degradation, and interfere with contrast agent function, as well as introduce other factors that may adversely affect the preservation and/or contrast operations. Removal may be accomplished by using isotonic (phosphate-buffered saline, 0.9% saline, lactated Ringers solution, etc.), hypotonic (hypotonic saline, distilled or other water, etc.), or hypertonic solutions (hypertonic 2% saline, hypertonic 23% saline, saturated saline solution, etc.). Non-isotonic solutions can be used to adjust fluid content throughout the body, rupture vascular cellular components, kill or otherwise inactivate intravascular microorganisms (depending on the solution tonicity and microbial in question) and/or act as a preparation step for additional preservation steps and/or contrast agents.

In a specific embodiment of the present invention, vascular and tissue conditioning agents may be used to prepare the subject before, during, or after a vascular flush, preservation, or contrast administration to improve the preservation and/or contrast operations. Some conditioning agents may be given pre-mortem, as with heparin and other anticoagulants, vascular relaxing, or contracting agents, etc. to prepare the subject for the preservation and/or contrast operations. Other agents may be given pre- or post-mortem, such as single or combined products (trisodium EDTA, DMSO, sodium borate, propylene glycol, cosolvents, acidifying and alkalinizing agents, coloring products, etc.) to help remove vascular components, modify solution pH (making later steps more successful), soften tissues, create more natural or specific color (including ultraviolet) hues, and prepare for additional preservation operations and/or contrast agents.

Additional modifications to the preservation operations may be used for specific or general improvements to the preservation and/or contrast process and to improve overall outcomes including use of the cadaver, imaging, etc. One example is placing peripheral vascular catheters, cannulas, or tubing, either as a point of fluid drainage or perfusion. Such placing of additional catheters, cannulas, or tubing peripheral (feet, legs, arms, hands, wings, tails, etc.) to the primary site of infusion may improve circulation of fluids to and/or from the more distant sites. Additionally, peripheral sites may be cut (usually for drainage) to provide a single (or multiple) egress site(s) or to encourage circulation to more distant areas.

In another step, naturally occurring or artificial obstructions, implants, etc. may be removed or added. For example, a major vessel may be clogged with a simple atheromatous plaque that may be removed via a surgical approach (and later closure) to the affected vessel. Similarly, a vessel may be clogged with an implanted vascular stent that could be removed via a surgical approach (and later closed) to the affected vessels. Alternatively, vascular clamps or surgical hardware may be added to demonstrate the effect that such additions have on blood, lymphatic, air, or other flow, imaging artifacts, etc. Artificial lesions, such as lacerations, aneurysms, or the like may be induced for teaching, research, or other purposes.

Some natural and artificial components may interfere with the preservation, contrast operation, and/or purpose of the cadaver and require removal for optimal results. For example, metallic hardware may need to be removed because it may cause artifacts or otherwise interfere with imaging operations. In yet another example of a modification, the cadaver may be partially dissolved to improve aspects of the preservation or contrast operations or to improve the intended outcome and use of the cadaver. As another example, acetone may be added to flush components to reduce the total body mass of adipose tissue regionally or systemically to reduce size, prepare tissues for select studies, and more. In an alternate example, the cadaver may be given excess intravenous fluids at higher than expected pressure in an effort to distend the extravascular and interstitial spaces to better separate tissues and improve stained components, as shown in FIG. 1.

The amount of elapsed time from cadaver preparation (flushing, conditioning, preservation, modifications) to perfusion, diffusion, topical exposure, soaking, and other operations of contrast agent staining can also play a role in outcome. Ideally, the time from death to preparation, preservation, contrast administration and ultimate utilization should be minimized. One critical step is from the time of death to cadaver preparation and preservation. Well-documented post-mortem changes have been previously reported and highlight the need to quickly prepare deceased subjects. For example, lividity (gravity-dependent blood pooling) is one of the first post mortem changes noted after irreversible cardiac arrest. As another example, rigor mortis often follows death within several hours. As time progresses, protein degradation and increased ammonia lead to loss of rigor mortis. Burkhard Madea, Methods for Determining Time of Death, 12 Forensic Sci. Med. Pathol. 451-485 (June 2016). Unless the cadaver is properly flushed in a timely manner, post-mortem changes, such as lividity, rigor and loss of rigor, can become permanent and adversely affect tissue disposition through degradation, preservation, and contrast perfusion. Adverse effects, such as lividity, may be alleviated by altering the position of the cadaver, applying digital pressure, massage, etc., and should be accounted for during cadaver preparation and contrast agent administration.

Figure 2:
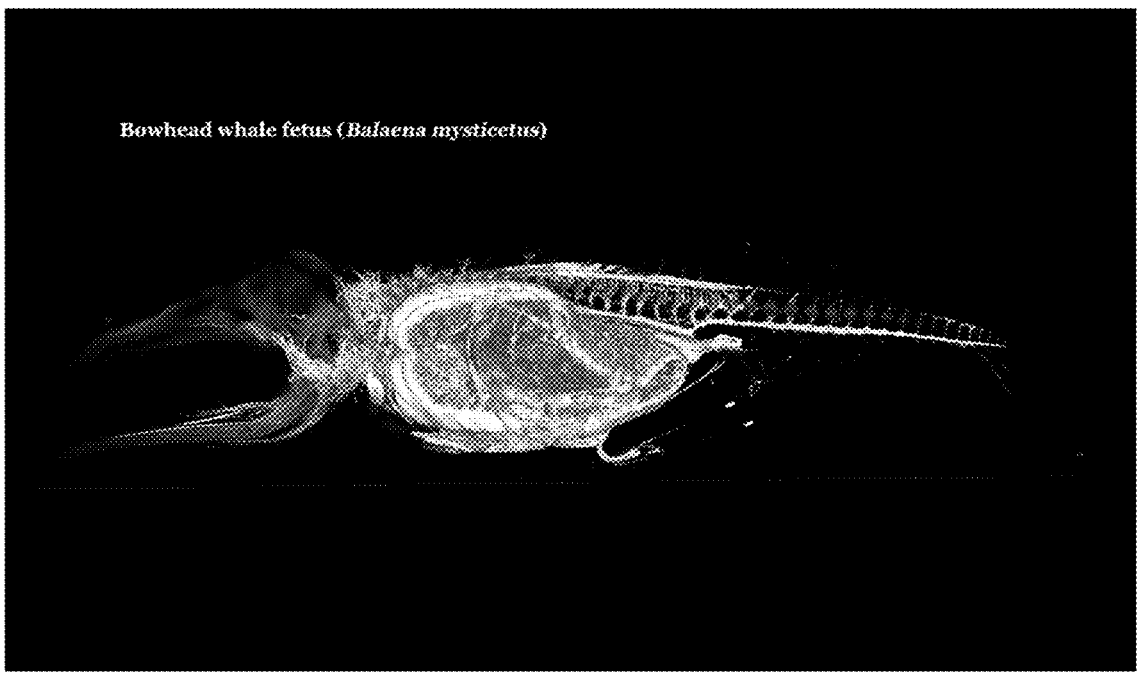
FIG. 2 is a CT-generated image of a bowhead whale (*Balaena mysticetus*) fetus tissue stained with a contrast agent in accordance with embodiments of the present invention.

Another critical phase is from the time of cadaver preservation, with or without preparation and/or conditioning, to contrast agent administration. Ideally, regional or whole-body contrast agent(s) is/are administered within 24-48 hours after the preservation operation. Preservatives, depending on the agents used, can alter anatomy and/or interact with contrast agents, affecting the contrast agent administration operation. For example, preservatives may cause shrinkage, adherence, stiffening, etc. of blood vessels which may adversely affect flow of intravascularly administered contrast agents. As another example, compounds present in the flush, conditioning, and/or preservative operations may interact with the contrast agents. For example, formaldehyde causes protein cross linkage of protein-based contrast agents that may contribute to premature solidification or other adverse effects. In many cases, the cadaver may need to be flushed with non-reactive fluids, such as isotonic fluids, to remove potentially reactive compounds prior to the addition of contrast agents. Not all cadavers may be treated with contrast agents within 24-48 hours after preparation, conditioning, and/or preservation. FIG. 2 shows that contrast perfusion with a barium-based contrast agent (e.g., BRITEVU®) may be used decades after flush and perfusion with 10% formalin administration intravenously and whole cadaver submersion. In specific inventive embodiments, the contrast agent may be a phenolic containing agent such as phenol. In specific inventive embodiments, the contrast agent may be nearly or completely non-toxic (to the personnel working with the agents and the environment and does not trigger significant health or other adverse claims) such as saturated salt-solution products.

Some cadavers may be frozen shortly after death prior to preparation, conditioning, and/or preservation and/or perfusion with or without diffusion, topical exposure, soaking of contrast agents, etc. Frozen cadavers are not ideal due to effects such as freeze and freeze-thaw artifacts, tissue and vasculature fractures that damage the subject, etc. The degree of freeze-type damage depends on multiple factors, including condition of the cadaver prior to freezing, freezing temperature, duration of time frozen, etc. However, frozen-thawed cadavers may also be used for tissue preservation (freezing is a form of tissue preservation, but may not be suitable for concurrent cadaver use) and subsequent contrast perfusion using methods described above (see FIG. 3).

Once the cadaver is properly prepared and preserved, the subject can then be perfused with either single or multiple contrast agents. These contrast agents may include diffusible and non-diffusible agents that are delivered via a perfusion method. Additionally, some agents (especially those that are diffusible) can be administered topically, or the subject can be submerged in the contrast solution. With proper preparation, the vascular system should readily accept the appropriately used contrast agent(s) (see FIGS. 4A-4B, 5A-5B, 6A-6B, and 9D).

As discussed in relation to the cadaver preparation and preservation operations above, the contrast agent can be delivered via the same or similar route(s). This includes adding, or using already added, peripheral (to the site or sites of primary vascular access) catheters, trocars, or lacerations, to other blood vessels or general soft and hard tissue regions. Depending on the preservation operation used, cadaver purpose, etc., the cadaver may be stored (cool, cold, frozen, room temperature, etc.) with or without additional preservation chemicals or processes or immediately used. Cadavers may be used for imaging (CT, X-ray, MRI, ultrasound, photography, etc.), procedures (practice surgery, anatomy discovery, research, forensic work, tissue histology, etc.), display, and more (see FIGS. 7A-7B and 8A-8B).

As previously noted, co-pending U.S. application Ser. No. 16/831,688 discloses an intravenously, immersibly, or topically delivered composition that can be used to image soft and/or hard tissue components of a subject using diffusible and perfusible agents capable of differentially staining an entire subject and the subject's various component/tissue types, as well as corresponding structures of insects, plants, and fungi. Inventive embodiments of this composition use carrier agents that make diffusible and perfusible agents capable of differentially staining the entire subject and its various component/tissue types. The use of a carrier agent promotes delivery of the contrast agent.

Figure 11:
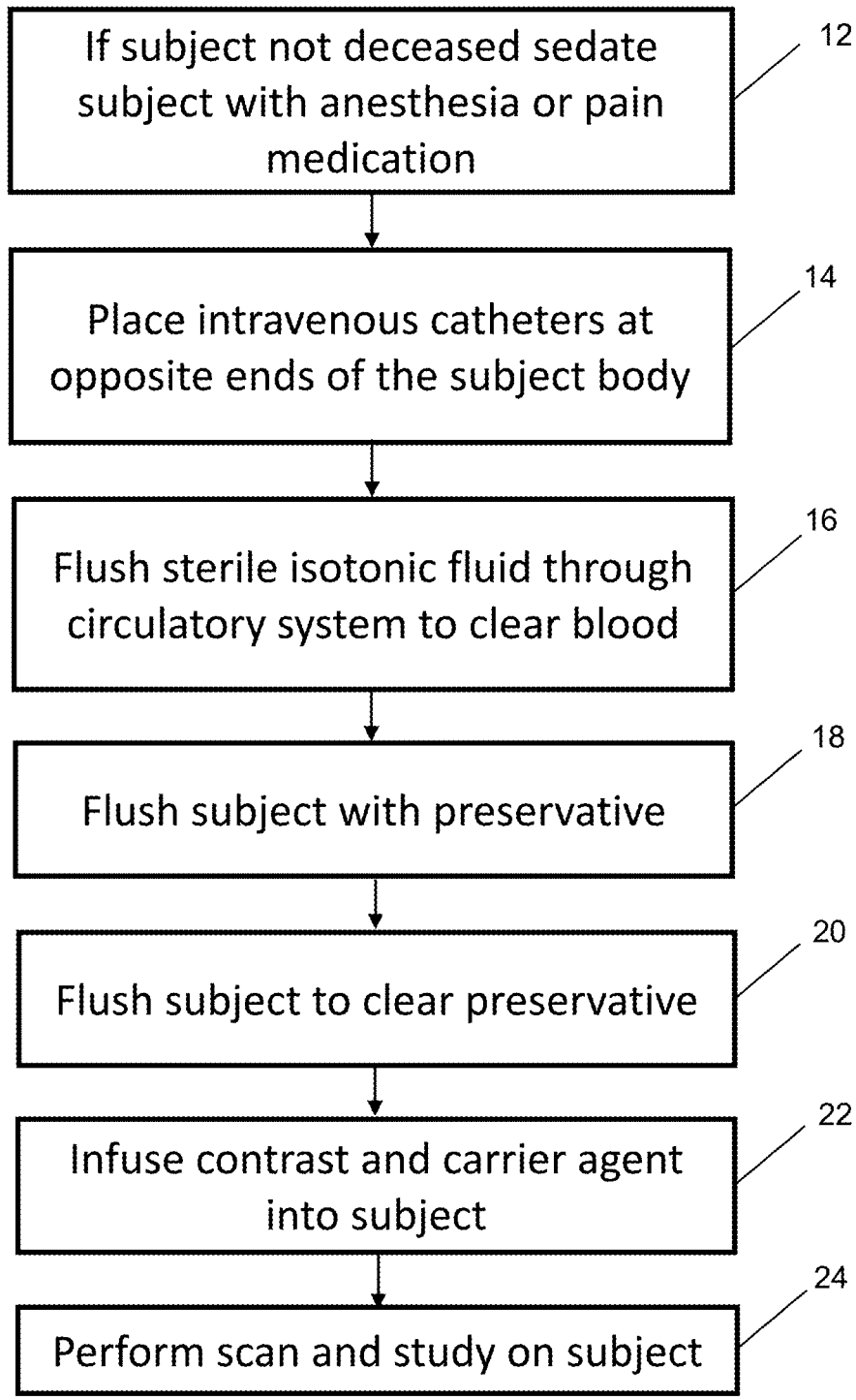
FIG. 11 is a flowchart showing an embodiment of the inventive process that preserves a subject and then uses an imaging contrast agent.

Reference is now made to FIG. 11, which is a flowchart 10 showing an embodiment of the inventive process that preserves a subject and then uses an imaging contrast agent. Operation 12 places a subject under anesthesia or heavy sedation or uses a cadaver with or without the blood components already flushed out, where the subject may receive anticoagulants and other chemicals as a step prior to flushing. Operation 14 then places and secures a first, single, or multiple, intravenous (IV), intraarterial (IA), intralymphatic (IL), intrarespiratory (IR), intracardiac (IC), or other intrachamber or system (OIC) catheter(s), trocar(s), tubing(s), etc. (collectively referred to as "catheter" or "catheter[s]"), and a second or multiple IV, IA, IL, IR, IC, OIC catheter(s) near or at opposite ends of a vessel or system in the body of the subject, with or without ligating or occluding a section of the vessel between the first, single or multiple, IV, IA, IL, IR, IC, OIC and the second or multiple IV, IA, IL, IR, IC, OIC catheter(s), with or without rolling, turning, flexing or otherwise moving the subject during all following actions that are performed to improve fluid circulation.

Operation 16 then flushes the subject with an isotonic, hypotonic, or hypertonic solution with or without a conditioning and/or preservative fluid through a circulatory, lymphatic, respiratory, or other system of the subject containing the vessel as a preparatory action such that most of the blood and/or other products contained within the subject's system are removed from the subject.

Operation 18 then flushes a preservative (with or without additional conditioning agents) through the circulatory, lymphatic, respiratory, or other system of the subject containing the vessel as a preservation operation, which also flushes and/or lyses blood products and preserves or fixes the subject such that natural degradation may be delayed or stopped.

Subsequently, with or without flushing an isotonic, hypotonic, or hypertonic solution, with or without a preservative fluid, operation 20 performs an additional fluid flush through the circulatory, lymphatic, respiratory, or other system of the subject containing the vessel as a post-preservation operation so that any remaining blood products contained within the system are removed from the subject. The system being flushed is thus cleaned of preservative that might interact with the contrast agent.

In operation 22, the subject is subsequently infused or perfused with a contrast agent or other agent, such as a carrier agent, that can enhance visualization using an imaging modality such as CT, MRI, radiography, ultrasound, photography, thermography, etc., into the first or multiple IV, IA, IL, IR, IC, OIC catheter(s) or sites. The perfusion may be delivered manually or mechanically. This perfusion may be performed with or without capping the first or multiple IV, IA, IL, IR, IC, OIC catheter(s) and the second or multiple IV, IA, IL, IR, IC, OIC catheter(s) until the subject is fully perfused.

In operation 24, the subject is then stored cool, stored in preservatives, or stored at room temperature, for later use or for immediate use for being internally imaged or for being studied or for having procedures performed upon the subject.

Besides the operations shown in FIG. 11, other operations or series of operations are contemplated to prepare tissues or a subject for preservation and imaging using a contrast agent. Moreover, the actual orders of the operations in the flowchart in FIG. 11 are not intended to be limiting, and the operations may be performed in any practical order.

Embodiments of the invention use tissue/object staining properties of radiodense, MRI enhancing, photo-visible or other contrast agents combined with at least one carrier agent, with or without the addition of other enhancing agents that improve the penetration of the stain into the subject material. Embodiments of the intravenous composition may be used as a whole organism system perfusion to affect the entire subject, creating a density staining process that can be completed in minutes to hours to days. The whole subject perfusion results in rapid distribution of the stain, providing differential contrast that is even, changes over time, and can be visualized using advanced imaging techniques such as X-ray, CT, photography, MRI, and/or ultrasound.

Contrast agents are used to highlight specific structures to improve visualization. The fields of visualization include those made with simple observation up to advanced imaging such as with X-ray based technology, including CT scans, MRI, advanced photography, and ultrasound.

Embodiments of the inventive method differentiate between organ systems (cardiovascular, lymphatic, musculoskeletal, integumentary, nervous, sensory organs (eyes, tongue, ears, nose), etc.) as well as between cell layers, regions, and tissue layers (e.g., arteries, veins, layers of intestine) within an organ system itself. The inventive method also differentiates between tissue types within cancerous and other abnormal tissues. It is noted that staining intensity and subject "tissue" differentiation changes with time. As the stain diffuses into the tissue, the staining intensity changes over time. This change in intensity can be easily noted within the first 24 hours of perfusion. This feature allows users to concentrate on different tissues at different time points to achieve ideal tissue intensity characteristics that are neither over nor under saturated. The present invention addresses prior art difficulties as to uniformity of staining and length of time to image a subject, which could run weeks or months.

Carrier agents can singly, or in combination with other compounds, pass through cellular and tissue membranes. Carrier agents are used in the pharmaceutical industry to transport drugs through membranes that are otherwise impermeable. They may also be used to deliver products through skin and other tissues. Carrier agents according to the present invention are used on biologic and non-biologic subjects. Carrier agents operative herein include: DMSO, urea, and alcohol (e.g., ethanol and isopropyl alcohol), as well as 1-dodecylazacycloheptan-2-one (Azone), which is used to deliver drugs via a percutaneous route. See Richard B. Stoughton, *Enhanced Percutaneous Penetration With 1-dodecylazacycloheptan-2-one,* 118 Arch. Dermatol. 474-477 (July 1982). Parhi et al. teach that "Numerous class[es] of novel compounds have been evaluated for penetration enhancement activity, including soft enhancement for percutaneous absorption (SEPA), for example, 2 N-nonyl-1,3-dioxolanes, N-acetyl[ ] prolinate esters (such as pentyl- and octyl-N-acetyl[ ] prolinate), alkyldiloxanes (e.g., 1-Alkyl-3-b-D glucopyranosyl-1,1,3,3-tetramethyl disiloxanes), trans-carbam (such as 5-(dodecyloxycarbonyl) pentylammonium-5-(dodecyloxycarbonyl) pentylcarbamate), iminosulfurane (like N-hexyl,N-benzoyl-S,S-dimethylimino-sulfuranes), capsaicin derivatives (e.g., nonivamide), cinnamene compounds (such as cinnamic acid, cinnamaldehyde, etc.), terpenes (like clove and basil oil) and synerg[i]stic combination of penetration enhancers (SCOPE)." Rabinarayan Parhi et al., *Novel Penetration Enhancers for Skin Applications: A Review,* 9 Curr. Drug Delivery 219-130 (March 2012). Cell-penetrating peptides have also been used as tissue carrier agents and are being studied for processes as complex as gene transfection. See Chanuk Jeong et al., A Branched TAT Cell-penetrating Peptide as a Novel Delivery Carrier for the Efficient Gene Transfection. 20 Biomaterials Research., Article 28 (September 2016). Other products such as chitosan nanoparticles (CS-TPP-NPs), DMSO, hyaluronic acid-transethosomes have all been shown to have potential as carrier/transporter/drug delivery agents. See Anissa Tazrart et al., *Skin Absorption of Actinides: Influence of Solvents or Chelates on Skin Penetration Ex Vivo,* 93 Intl J Radiation Biology 607-616 (June 2017); Nursyafiqah Sahrum Ayumi et al., Polymeric Nanoparticles for Topical Delivery of Alpha and Beta Arbutin: Preparation and Characterization, 9 Drug Delivery and Translational Res. 482-496 (March 2018); Silvia Franzé et al, *Hyaluronan-decorated Liposomes as Drug Delivery Systems for Cutaneous Administration,* 535 Int'l J. Pharm. 333-39 (January 2018). Various alcohols, urea, glymes, and glycols are also operative herein, alone or in combination as carrier agents.

It is further noted that many chemicals have been used with carrier agents to provide effects at both the local level and the system level. Some chemicals are used for local effects such as deep penetrating skin products that treat dermatologic disorders (triamcinolone acetonide plus a carrier agent). Other chemicals can also be applied via the same route (skin) and may be used to treat systemic disorders (testosterone plus a carrier agent used for the treatment of female sexual dysfunction). See Mark R. Prausnitz and Robert Langer, *Transdermal Drug Delivery,* 26 Nature Biotechnology 1261-1268 (November 2008). A non-exhaustive list of drugs used in combination with carrier agents include acyclovir, insulin, human growth hormone, granisetron, influenza vaccine, heat labile enterotoxin of *E coli* and much more. Some of these agents target nerve receptors in known (and some unknown) mechanisms and illustratively including products such as lidocaine, buprenorphine, fentanyl, and rotigotine. Id. These examples only serve to show the diversity of classes of agents (hormones, pain medications, antivirals, vaccines and more) that can be combined with carrier agents.

In certain inventive embodiments, when enhancing agents such as those that affect receptors, on/off switches, etc. (nerves, hormones, binding proteins, etc.) are delivered to the site of action new products, actions and more can be generated (proteins, immune responses, open/close action potentials, nerve impulse initiation and signaling, etc.). Receptors may be found in organic and inorganic structures. By delivering some compounds (such as via carrier agents and better dispersion methods), there are opportunities to create a response, product, etc. that can be further acted upon by the addition of another product introduced into the system (via carrier agent, diffusion, perfusion, or other dispersion method). Embodiments of the inventive process may be "laddered" to create a multitude of responses that would not otherwise be possible without exposing the target tissue to these specific agents.

Examples of enhancing agents include vasodilators and vasoconstrictors, atropine, N-acetyl aspartate, choline, epinephrine, norepinephrine, opioids and their derivative compounds, creatine, myosin, cholinesterase compounds, anticholinesterase compounds, paralytic agents, perfluorocarbon-based oxygen carriers, lactate, beta blockers, antimicrobials, calcium channel blockers, antidepressants, acetylcholinesterase inhibitors, barbiturates, non-opioid narcotics, non-steroidal anti-inflammatory agents, enzymes and enzyme inhibitors, cell specific markers, and combinations thereof.

Embodiments of the intravenous imaging composition that use diffusible and perfusible agents may be used with different vascular conditioning agents to improve the distribution of the contrast agent and tissue type being stained. For example, a water-soluble vascular conditioning agent such as Dodge METAFLOW pre-tissue contrast stain gives a different contrast stain profile compared with lipid stripping products such as Dodge PROFLOW.

Prior to perfusion with the embodiments of the contrast and carrier agents, the vascular system may be conditioned to improve perfusion. For example, agents may be water based (water plus Dodge METAFLOW or PROFLOW plus or minus RECTIFIANT, for example) that are used to break up blood clots, adjust for minerals in added water, and aid in removal of clots of deceased subjects. Other compounds illustratively including anticoagulants (heparin, warfarin, etc.) may be added pre-mortem to aid in the removal blood and/or prevent blood clotting (which also aids in the removal of blood). Additionally, hypotonic to hypertonic agents may be used to rupture blood cellular components thereby improving the removal of blood. By removing blood clots, the vascular system becomes more open or otherwise penetrable by the contrast and carrier agents. Additionally, blood components may interact with certain contrast agents (such as silver-based or barium-based compounds). It is best to remove as many blood components prior to perfusion as possible to reduce adverse reactions. This in turn results in better perfusion and more even diffusion across the vascular system and into target tissues.

In some inventive embodiments, additional agents used to reduce odors and/or act as chemical disinfectants may also be added to the contrast solution that do not significantly detract from the contrast staining abilities. Odor-reducing agents may be added to reduce unpleasant smells that may be associated with the chemical composition by itself and/or reaction with the perfused subject's (biologic and/or non-biologic) makeup. These compounds may include natural and artificial scents and flavorings, disinfectants, antimicrobials, etc., such as vanilla extract, orange (or other citrus) extract, urea, and alcohol.

Embodiments of the invention use tissue/object staining properties of radiodense or other stains combined with one or more carrier agents with or without the addition of other enhancing agents that improve the penetration of the stain into the subject material and/or targets specific cells, tissues, structures, etc. Embodiments of the inventive process may be used as a whole or partial system perfusion to affect the entire subject creating a density staining process that can be completed in minutes to hours. The whole or partial subject perfusion can also result in rapid distribution of the stain providing differential contrast that is even, changes over time, and can be visualized using advanced imaging techniques such as X-ray, CT, MRI, photography, and/or ultrasound.

For animal subjects, including mammals, birds, reptiles, amphibians, fish, and invertebrates, embodiments of the inventive method may be used to inject imaging agent into the vascular system, lymphatic system, respiratory system, or other potential spaces for local, regional, or whole-body perfusions. Alternatively, the subject (local, regional, or whole) may be soaked in the tissue stain solution. Alternatively, the solution may be injected (via a needle and syringe for example) into the subject for local, regional, or whole body diffusion staining. The subject may also be subjected to increased pressure, as with a hyperbaric or other chamber, to increase the rate of diffusion of perfused or direct contact staining agents.

Embodiments of the invention demonstrate the use of a carrier agent used in combination with contrast agents and other drugs in order to improve the ability of diffusible and perfusible agents to provide contrast within one or more tissue/components of a subject to be better visualized using simple (simple visualization, dissection, photography, etc.) to advanced imaging techniques (CT, MRI, ultrasound, etc.). The diffusible agents can be delivered throughout a subject like a perfusible agent. The diffusible agents can be combined with drugs, chemicals, and other substances and delivered topically or via direct contact to create local to systemic effects. Drugs, chemicals, and other substances can be delivered via a perfusion method with or without a diffusion product to affect different subject tissues/components in a therapeutic, diagnostic, investigative, or other manner. This procedure can be used on plants, animals and non-biologic subjects.

In specific inventive embodiments, metallic compounds illustratively including silver nitrate may be combined with a carrier agent, solubilizing, or permeabilizing agent illustratively including alcohols, DMSO, glycols, glymes, urea, and combinations thereof; and perfused into the subject to highlight specific structures such as nerves. In one example, silver nitrate (2.5-50%) can be combined with a carrier agent (silver nitrate 2.5-90% to carrier agent v/v) and perfused into or applied to the subject. The combined product can be perfused into the cardiovascular system. The carrier agent then carries the silver nitrate through the vascular system and into the target tissues. Due to the density of the metallic compound, the targeted tissue is then "visible" using X-ray technology such as with CT scanning.

Embodiments of the inventive method provide imaging to completely highlight the cardiovascular and other bodily systems using low-cost, relatively non-toxic and easy-to-administer materials that can be readily viewed using CT or standard radiographs and produce high quality images. Embodiments of the method provide imaging of completely perfused entire animal subject, rather than a portion as with prior art compositions, such as MICROFIL® (Flow Tech Inc.). As used herein, animal subject refers to a mammal, a reptile, an amphibian, a fish, an invertebrate, or an avian. Embodiments of the compositions used in the inventive process flow through the subject vascular system without clogging vessels, arteries (arteriole and venule), or capillaries. The CT or MRI slice thickness and resolution determines the size of the vessels visualized. Scanning can begin immediately after perfusion with an embodiment of the inventive method is complete or perfused tissues can be harvested and stored in formalin, other preservatives of fixative, and stored, with or without cooling, for later scanning. By adding dye to the carrier agent, visualization of small (and large) vessels can be significantly improved during gross dissection or using UV light, photography filters, etc.

Embodiments of the inventive method allow for creation of gross and digital (with the aid of CT/radiography/MRI/photography/ultrasound) vessel or tissue visualization for anatomy study. Study may include classroom up to research study, including forensics. "Study" includes anything where the anatomy of the study subject needs to be understood. Vascular anatomy knowledge gives one shape and size of organs, shunts and other vascular anomalies, tumors and other tissues. Soft tissue, not just vascular, anatomy also serves to provide valuable information. This information is vital to understanding basic anatomy, biology and behavior of tissues.

Subjects infused by embodiments of the inventive method may be used to create digital images that are used to help develop other imaging products and studies. For example, performing MRI time-of-flight on selected animals is conducted first, and then followed up with the contrast product injection and CT. The contrast CT images may be used as a standard to help in understanding what is being seen on the time-of-flight study (non-invasive means to look at blood vessels). As a result, a match between the two images (CT and MRI) can be made, and information from the contrast CT may be used to improve upon the time of flight procedure. The same can be true with developing other imaging processes where an accurate vascular or tissue map (as created with embodiments of the inventive method) is needed for comparison.

EXAMPLES

Example 1

An embodiment of the inventive method is shown in FIG. 1 with a preserved cadaver that is tissue contrast stained such that the interstitium is highlighted following CT-scanning.

The interstitium is considered a new organ, but it has been difficult to study due to its location and collapsible nature. See Petros C. Benias et al., *Structure and Distribution of an Unrecognized Interstitium in Human Tissues*, 8 Scientific Reports 1-8 (March 2018). In reference to the interstitium, "the existence, location, and structure of larger inter-tissue and intra-tissue spaces is described only vaguely in the literature." Id.

The interstitium is notoriously difficult to identify without damaging the tissue. With the inventive methods described in this application, the interstitium can be visualized.

An 89-year-old woman passed away and was preserved seven days later using multiport vascular flushing and soft tissue short-term preservation (using 3 L distilled water and 9 L of a salt solution). This process removed intravascular blood and provided for short-term preservation. Next, the cadaver was perfusion flushed (also via multiple vascular points of entry) with 15 L of BRITEVU®, a proprietary tissue radiodense stain. The process allowed for multiple whole-body CT scans over 24 hours and highlighted soft tissue structures as radiodense.

As shown in FIG. 1, the interstitium is readily visible as a trabecular network between the skin and the thigh muscles. The femurs can be seen at the center of each leg. The cadaver was systemically IV perfused with an iodine-based stain, an aforementioned carrier agent, alcohol, and two odor reducing agents one week after death, followed by a coronal view CT scan 1-hour post-perfusion at a 0.625 mm resolution of the thighs.

While Benias, supra, described using confocal laser endomicroscopy of biopsied tissues to identify interstitial tissues, the methods described in this application allow for visualization of this tissue (or organ system, by some accounts) in situ, allowing for non-destructive study of the whole subject. This method further reveals the interrelationship between all tissues, a demonstration not possible with a biopsied segment.

Example 2

FIG. 2 illustrates imaging of a preserved bowhead whale (*Balaena mysticetus*) fetus. The fetus was recovered from a deceased bowhead whale cow and its vasculature was flushed, via the umbilical artery, with an unknown amount of 10% formalin. The whale was then stored in a large container filled with 10% formalin. Twenty-five years later, the fetus was removed from the formalin-filled container, flushed via the umbilical artery with 5.5 L 0.9% saline, and then flushed with 2.0 L BRITEVU®. The BRITEVU® filled fetus was then CT-scanned and placed back in the vat of formalin for continued long term storage.

Example 3

Figure 3A:
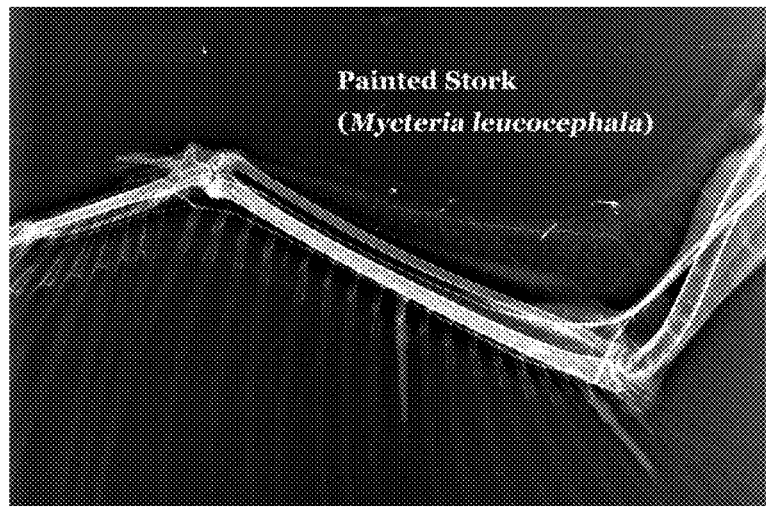
FIGS. 3A-3C are images of a painted stork made in accordance with embodiments of the present invention.
Figure 3B:
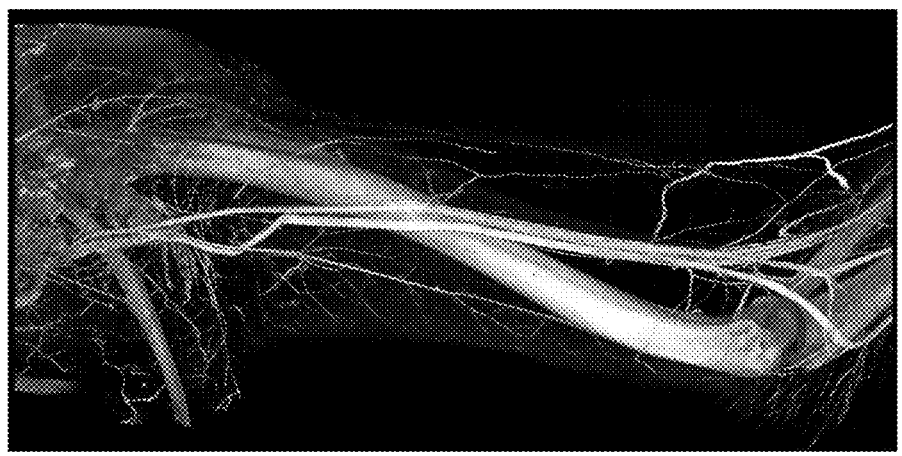
Figure 3C:
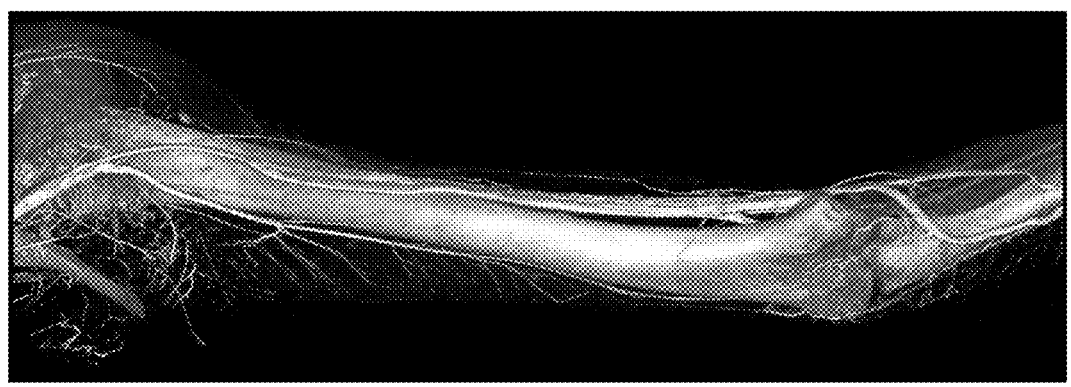

FIGS. 3A-3C illustrate imaging of a preserved painted stork (Mycteria leucocephala). The painted stork, which recently died of natural causes, was frozen for 3 days, thawed and then flushed via the brachiocephalic artery with a combination of 0.47 L of Lactated Ringers Solution plus 0.33 mL Dawn Ultra Platinum (Proctor and Gamble) to flush the vascular system and remove clots of the wing. This may constitute the flushing and preservation operations. One hour later, the limb vasculature was flushed with 116 mL of BRITEVU®. The limb was then submerged in formalin and stored for several months until CT-scanning could be completed. FIG. 3A shows a ventral dorsal radiograph taken the same day as the perfusion of the wing with vascular system highlighted with the BRITEVU® contrast agent. FIGS. 3B and 3C show the same wing CT-scanned at a resolution of 100 µm seven months post-perfusion with contrast agent. The vasculature is readily visible in FIGS. 3B and 3C.

Example 4

Figure 4A:
FIGS. 4A and 4B are sagittal MRI and transverse CT images, respectively, of a brain of a domestic pig made in accordance with embodiments of the present invention.
Figure 4B:
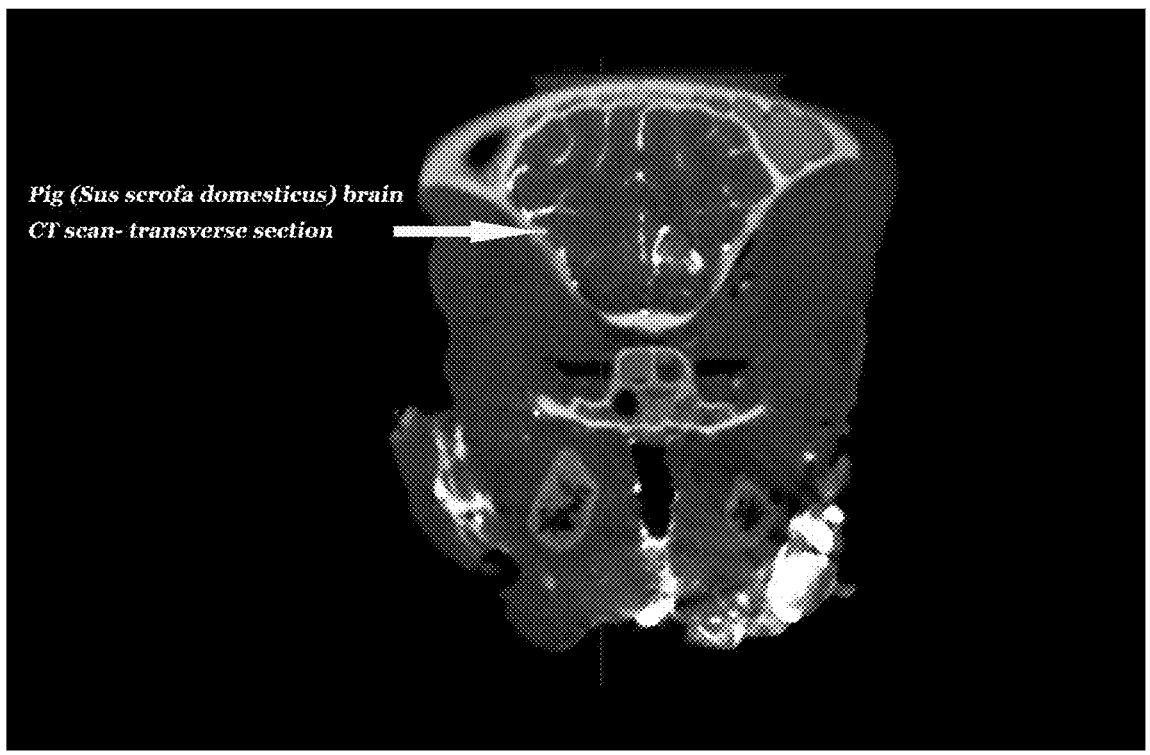

FIGS. 4A and 4B illustrate imaging of a preserved domestic pig (Sus scrota domesticus). An anesthetized pig was given a 1000 U/kg heparin IV 30 minutes prior to flushing. 2.4 L of phosphate buffered saline was flushed into a left jugular vein catheter, with fluid coming out an open left femoral artery catheter. Subsequently, a solution of 0.75 L distilled water and 0.25 L PROFLOW was flushed through the left jugular cannula. Next, 1 L of Dodge Freedom Art preservative was flushed through the left jugular catheter, followed by storage in a refrigerator for 14 days. FIG. 4A is an MRI scan of the brain at that time. Fifteen days later, the head was removed, preserving the left and right carotid arteries. The carotid arteries were each catheterized and flushed with a total of 420 mL of deionized water. Then, 300 mL of BRITEVU® was perfused through the catheters. The head was stored in the refrigerator. Thirteen days later (28 days post mortem), the head was CT-scanned (FIG. 4B is a transverse section view of the brain showing the "white" vasculature of the brain).

Example 5

Figure 5A:
FIGS. 5A and 5B are images of the chest of a subject.
Figure 5B:
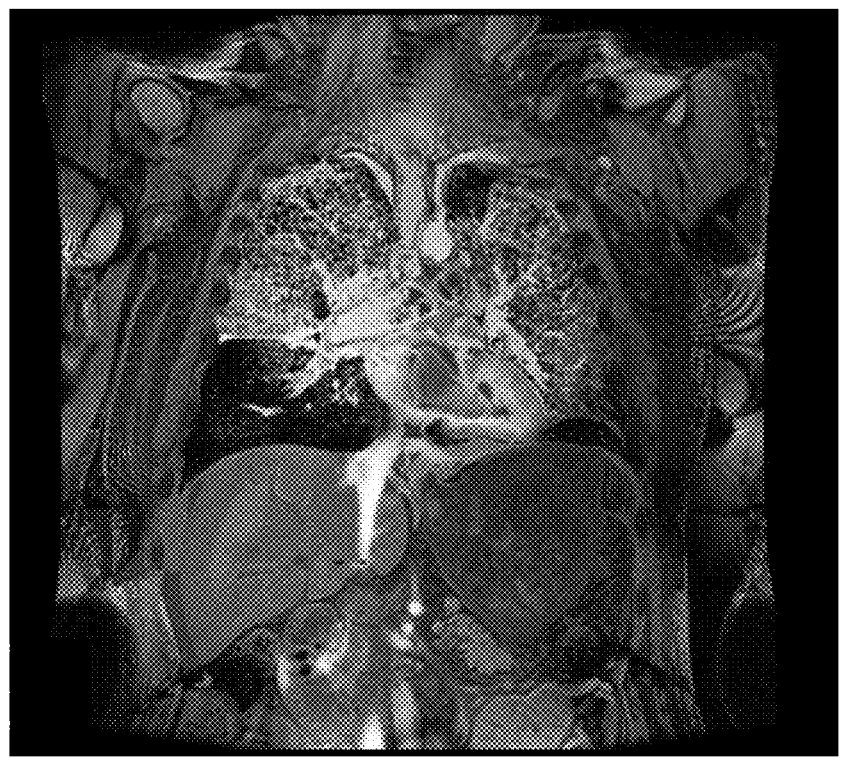
Figure 5C:
FIG. 5C is an image of the brain of the same subject, all made in accordance with embodiments of the present invention.

An embodiment of the inventive method is used to image a human chest and brain. FIGS. 5A and 5B both illustrate the chest of a subject, and FIG. 5C shows the brain of the same subject. The cadaver was "soft fixed" using a combination of preparation flush (distilled water, Dodge PERMAFLOW, and RECTIFIANT) and preservation flush (Freedom Art) and then perfused with a gadolinium-infused contrast solution containing BRITEVU®. FIG. 5A shows a coronal view (maximum intensity projection) of the chest with the vasculature as "white." FIG. 5B shows a coronal view (standard T1 MRI) of the chest with the vasculature as "white." FIG. 5C shows a sagittal view of the brain with vasculature evident as "white" in the T1 MRI scan.

Example 6

Figures 6A, 6B:
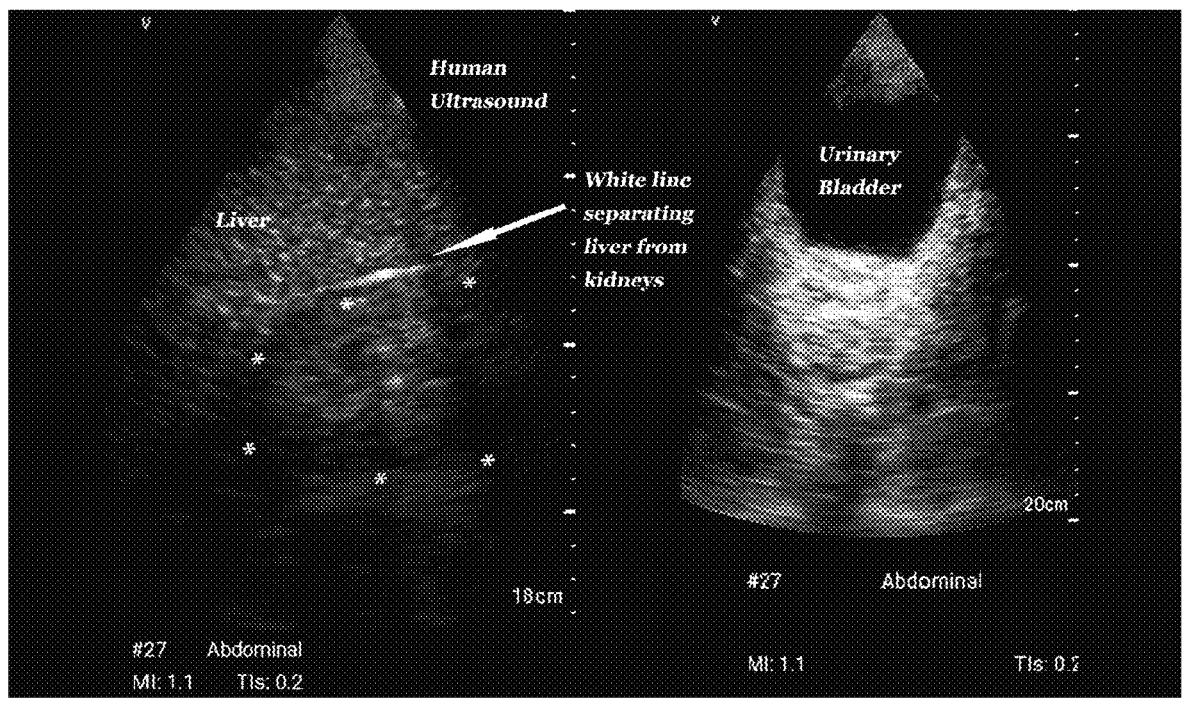
FIGS. 6A-6B are ultrasound images of a human cadaver made in accordance with embodiments of the present invention.

An ultrasound is performed on a human cadaver that has been preserved and perfused with a perfusible contrast agent in accordance with an embodiment of the inventive method. The cadaver was "soft fixed" using a combination of preparation flush (distilled water, PERMAFLOW and RECTIFIANT) and preservation flush (Freedom Art) and then perfused with BRITEVU® contrast agent. Because the contrast agent, BRITEVU®, is primarily water, and the vasculature filled, the BRITEVU® acts as positive contrast for the ultrasound study. The image of FIG. 6A shows the right upper abdominal quadrant view of the liver (top) and kidney.

The "white" line delineation in this Figure visually demarcates the liver from the kidney (outlined using asterisks (*)).

However, this is generally not possible in cadavers without filling the vasculature with an ultrasound positive contrast. The image shown in FIG. 6B is of the pelvic region and shows the urinary bladder "window." Again, this is usually not very visible in cadavers. However, it is here, due to filling of the urinary bladder and abdominal viscera vasculature filling with the contrast agent. Because of the inventive method, this cadaver was used for multiple imaging modalities (CT, MRI, and ultrasound), and for surgical training purposes that spanned several weeks.

Example 7

Figure 7A:
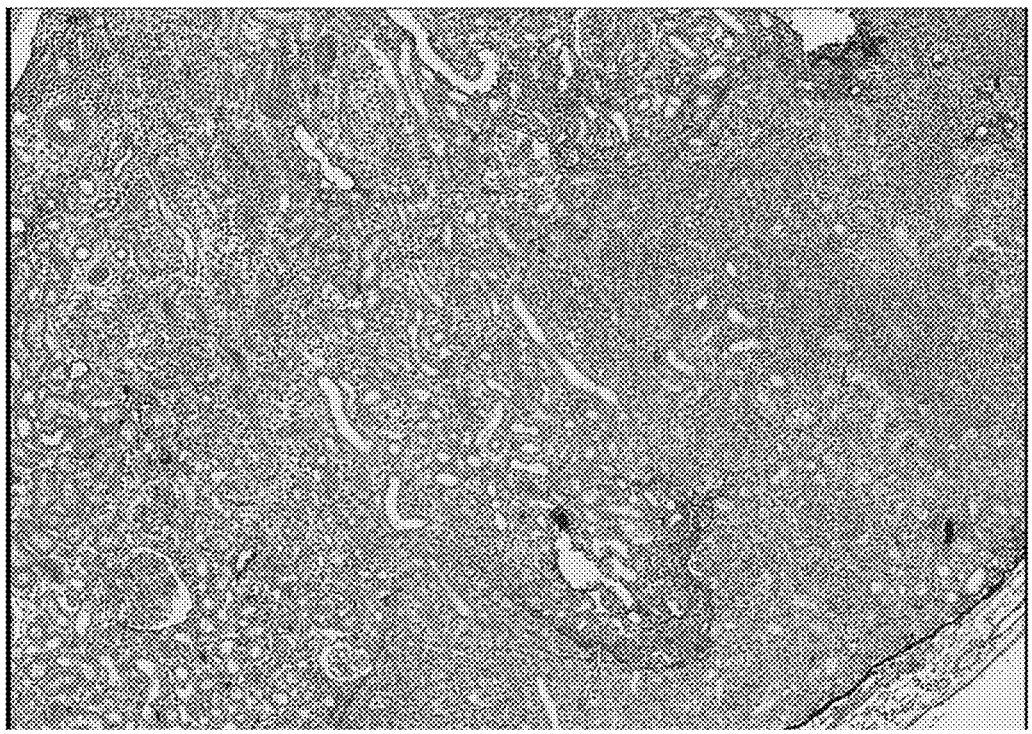
FIGS. 7A and 7B show a rat imaged with a contrast agent in accordance with embodiments of the present invention.
Figure 7B:
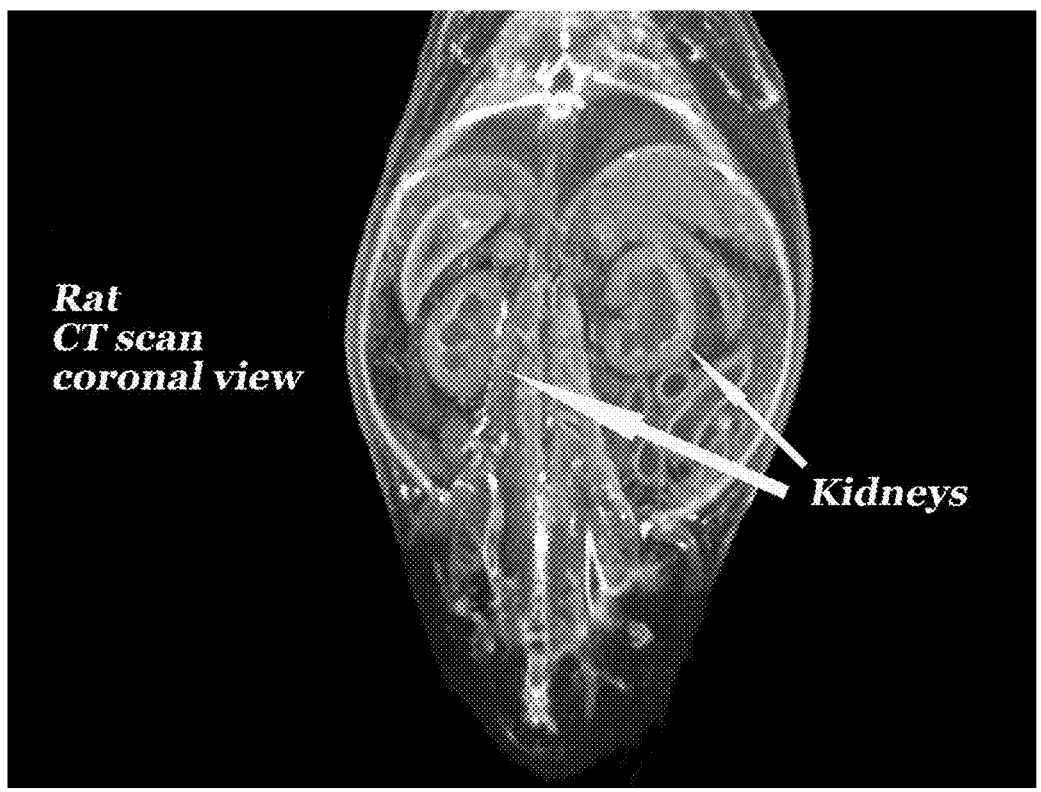

An embodiment of the inventive method is used to image a rat. The rat was perfused and flushed with saline, and the preservation method was combined with perfusible, diffusible tissue contrast. Five days after perfusion and without further preservation, tissue was collected for histology showing normal tissue architecture (FIG. 7A, showing cellular components of a kidney). The contrast agent can be visualized as "dark deposits." The architecture and cellular integrity was maintained without evidence of degradation. This demonstrates that the inventive method keeps cellular components intact while, in this case, a perfusible, diffusible contrast stain worked over a period of several days without compromising tissue integrity. In FIG. 7B, a CT scan at 200 µm resolution shows the coronal view of both kidneys (the same subject of FIG. 7A). The kidneys demonstrate differential staining as evidenced by varying degrees of contrast stain uptake, and were studied over a period of 5 days. This series demonstrates how the inventive method results in no detectable alteration to the contrast-stained organs, which is critical to studying cadaver tissues in a longitudinal manner.

Example 8

Figure 8A:
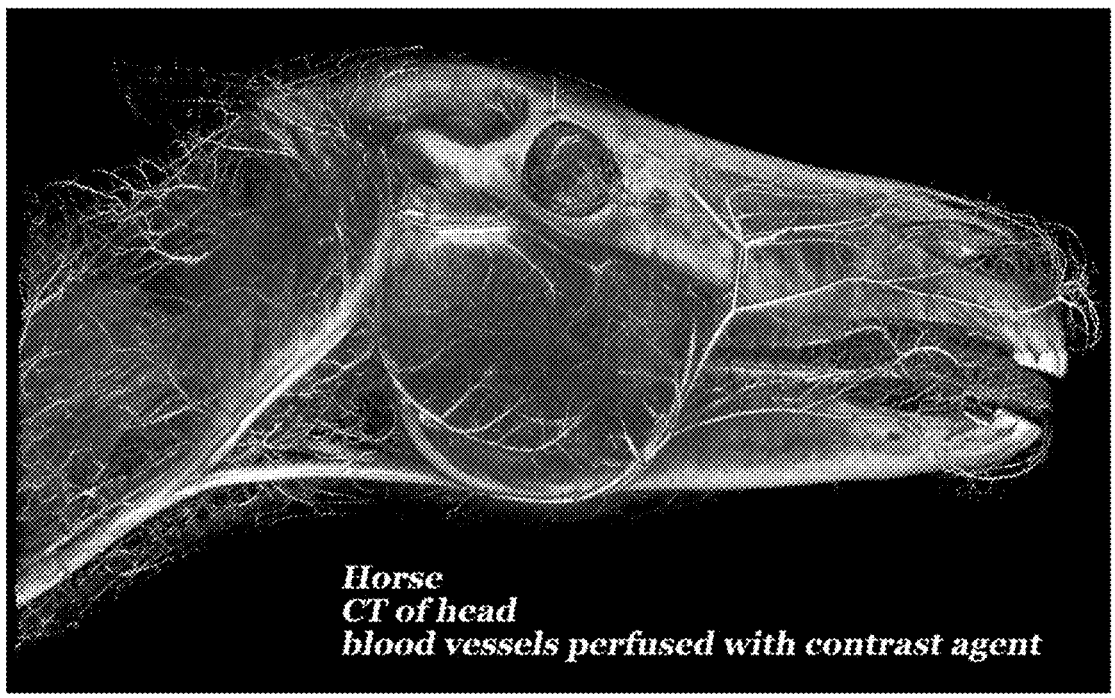
FIGS. 8A and 8B show a horse imaged with a contrast agent in accordance with embodiments of the present invention.
Figure 8B:
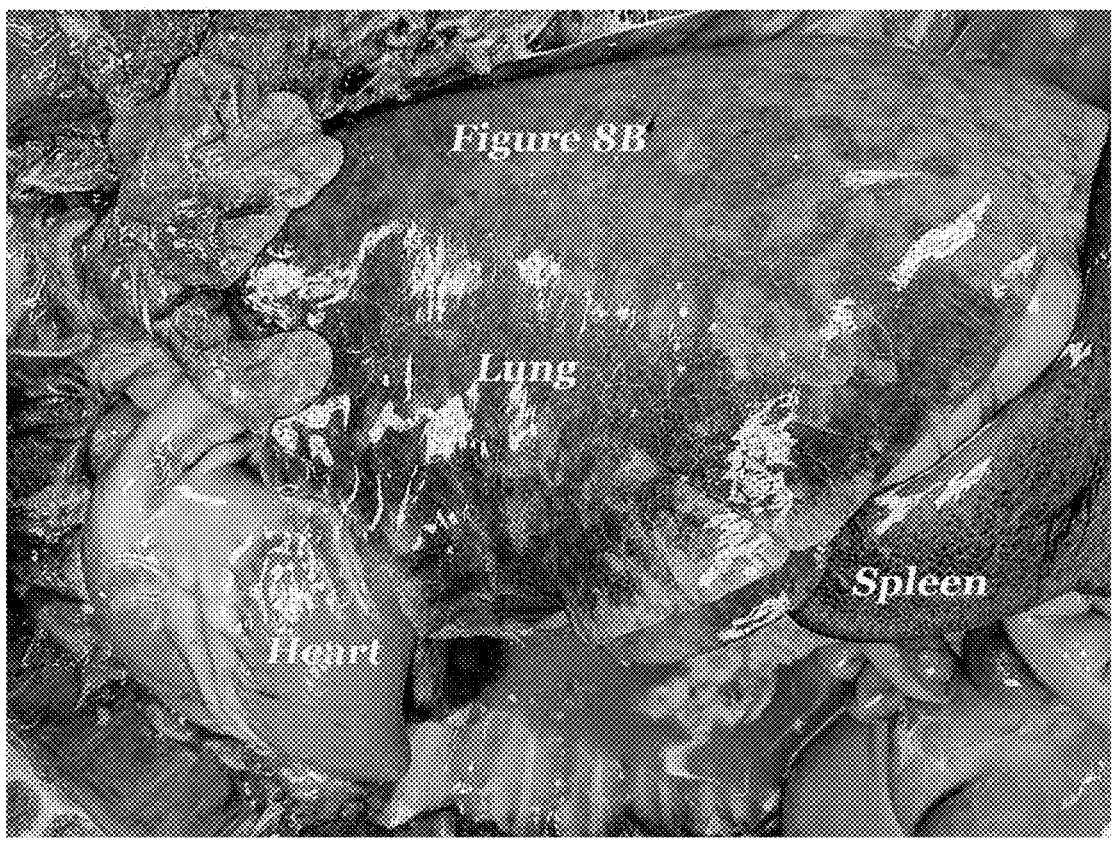

An embodiment of the inventive method was used to image a horse. The horse was flushed with vascular conditioning agents (PERMAFLOW and RECTIFIANT), distilled water, and then perfused with a "soft fix" preservation method (Freedom Art) via multiple vascular cannula sites, and drained via multiple vascular cannula sites. Eight hours later, the cadaver was flushed with distilled water and perfused with BRITEVU®. The soft-fixation method allowed for CT-scanning 8 days later and dissection of soft and life-like tissue. FIG. 8A shows a 200 µm resolution CT scan (sagittal view) of the head, with the blood vessels containing readily visible contrast agent. FIG. 8B shows the necropsy of this horse after preservation and contrast agent perfusion. The heart, lungs, and spleen are readily visualized and appear similar to fresh tissue. This demonstrates how preservation methods combined with contrast agents can increase the usable "lifespan" of the tissues, in this case for extended imaging studies, and can also make the tissues "life-like" and acceptable to perform procedures, surgery, etc., where this may otherwise not be possible due to rapid autolysis without some form of preservation.

Example 9

A Ross's goose (*Chen rossii*) was given a 1000 U heparin/kg body weight IV via a right jugular vein (inflow) catheter. A right medial metatarsal vein (outflow) catheter was placed for drainage. The goose was euthanized 20 minutes later and preserved with a combination of 60 mL PROFLOW, 30 mL RECTIFIANT and 410 mL distilled water. This was followed by 120 mL of an isopropyl plus glutaraldehyde mixture plus 200 mL of distilled water. Five m L/kg of ISOVUE®-370 was given via IV for a CT scan. The last step included a BRITEVU® vascular contrast systemic perfusion of 360 mL. The goose was CT-scanned with no contrast, with ISOVUE®-370 contrast, and with BRITEVU® contrast to create three unique studies with differential contrast amounts. The cadaver was then stored in refrigeration at 42° F. and necropsied 3 days later. Various tissues were collected and stored in 10% formalin and submitted for standard H&E histopathology.

Figure 9A:
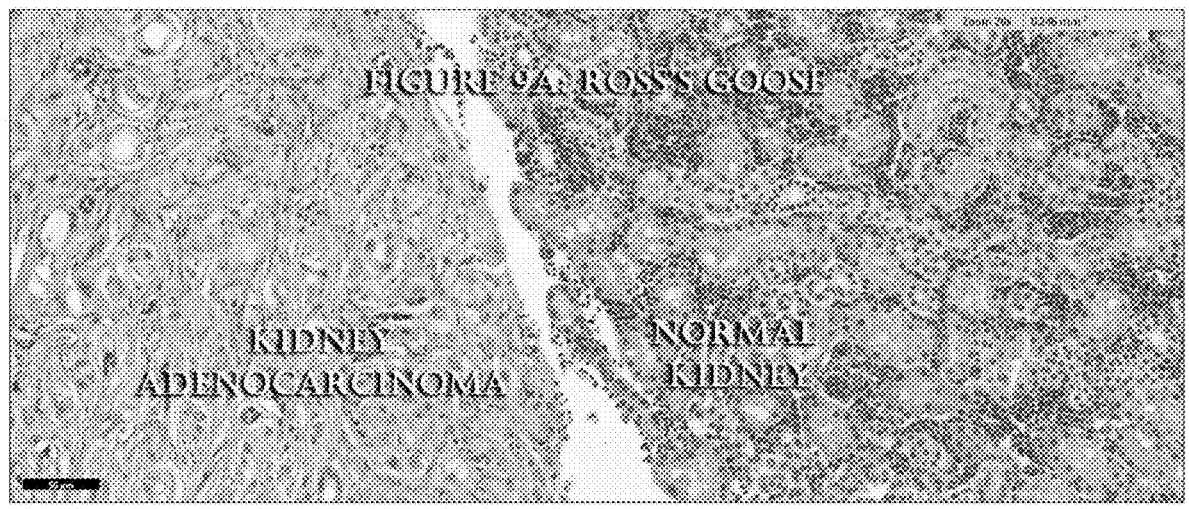
FIGS. 9A-9D show a goose imaged with a contrast agent in accordance with embodiments of the present invention.
Figure 9B:
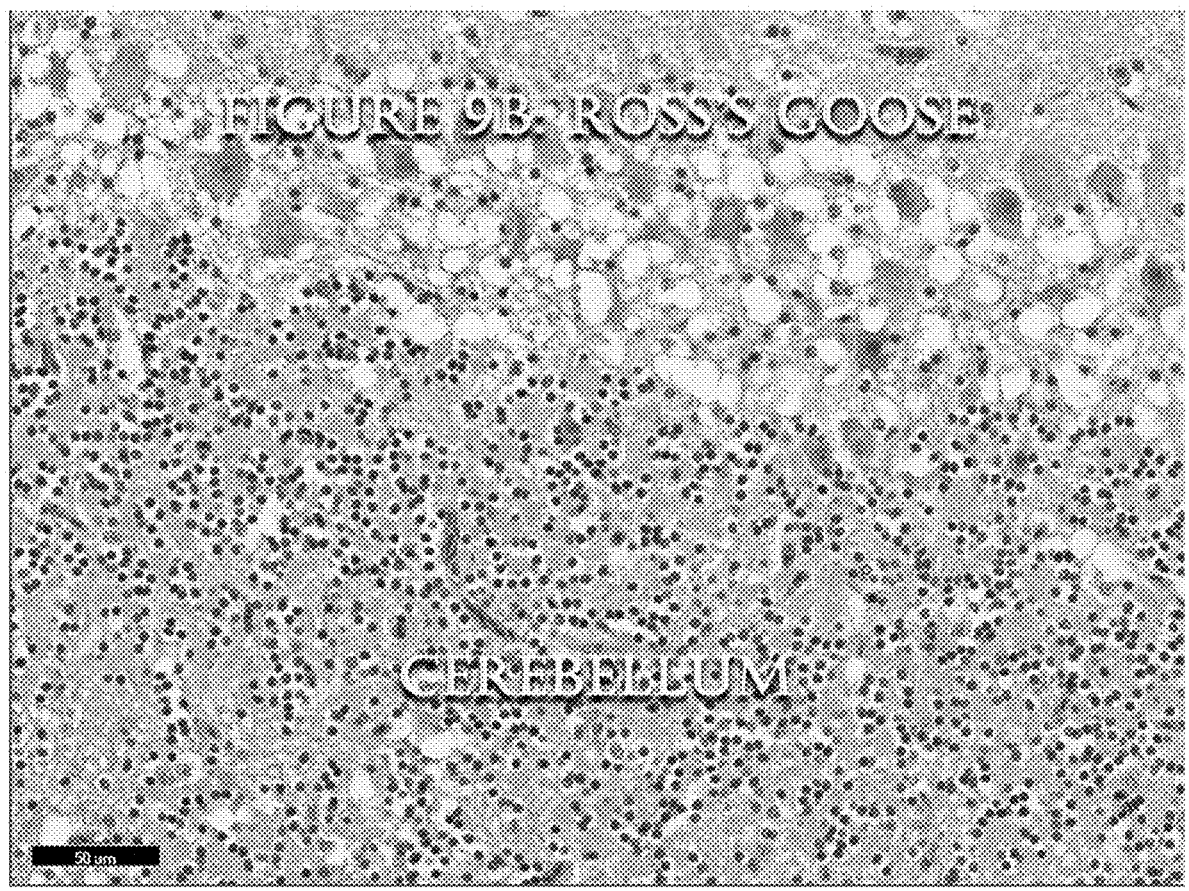
Figure 9C:

FIG. 9A shows well-preserved kidney histology and cancerous tissue (renal adenocarcinoma) adjacent to healthy kidney tissue. FIG. 9B shows well-preserved brain tissue (cerebellum). The brain rapidly degrades post-mortem, and the inventive method demonstrates how tissue can be preserved, without formaldehyde, alongside the administration of multiple different contrast agents. FIG. 9C shows liver tissue that ranges from normal to transitional to full granulomatous disease due to *Mycobacterium* species (aka tuberculosis), demonstrating preservation of granulomatous tissue due to tuberculosis alongside transitional and normal liver cells. In all three histology images, the tissues were collected and stored in formalin three days after death using the inventive method. The series demonstrates tissue preservation using non-formaldehyde-based products in the inventive process. Normal, cancerous, and infectious/inflammatory tissue were all well preserved, and each disease process was highlighted using contrast imaging.

Figure 9D:
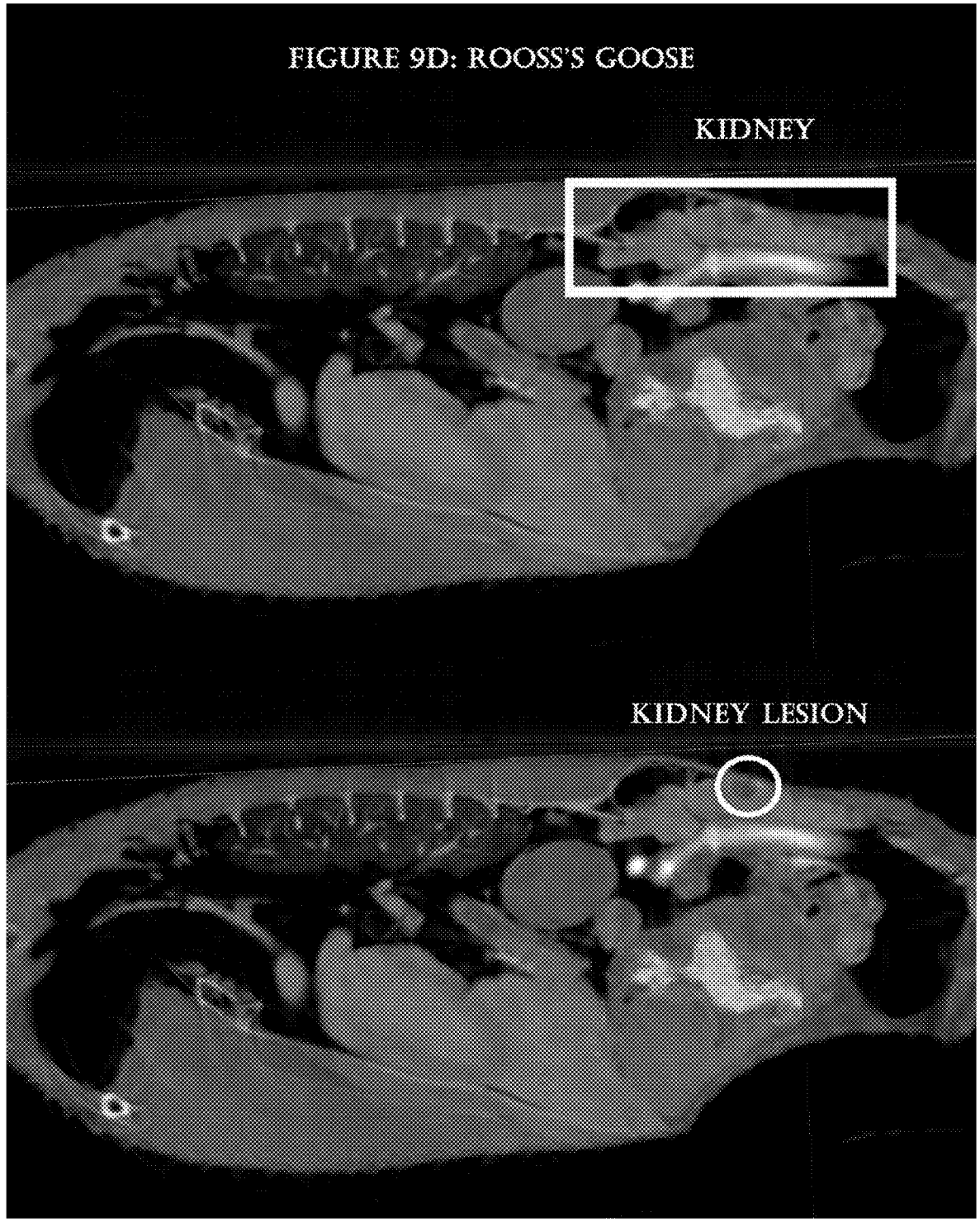

FIG. 9D demonstrates the use of an iodinated contrast agent, ISOVUE®-370, in the inventive method. The sagittal view of the body CT scan at a 200 µm slice thickness shows contrast throughout the bird's body. Of interest is the kidney in the rectangular area (top image), where in the dorsal middle region of the kidney (highlighted by the circle in the bottom image), there is a small circular area of decreased contrast. The highlighted area represents the renal adenocarcinoma described in FIG. 9A. This image demonstrates the use of the inventive method as a means to forensically identify specific lesions post-mortem using an iodinated contrast agent intended for live study.

Example 10

A 60-year-old male cadaver was prepared for preservation and radiodense contrast eight days after death. The cadaver was stored in a refrigerator at approximately 42° F. starting one day after death, and throughout the remainder of the study, except for times needed to collect samples and images. Two inflow cannulas were placed in the carotid artery, one directed superiorly and the other inferiorly. An outflow incision was made in the right jugular vein. 2.8 liters of PROFLOW, 1.4 liters of RECTIFIANT, and 17.0 liters of distilled water were infused into the cadaver, followed by a flushing of 5.7 liters of a mix of isopropyl alcohol and glutaraldehyde, plus 9.7 liters of distilled water. A mixture of 7.5 liters of BRITEVU® plus 9.5 mL of water-soluble fluorescein dye was then perfused through the cadaver. During perfusion, an ultrasound was performed to demonstrate flow of fluid through organs such as the kidneys, liver, and intestines.

Figure 10A:
FIGS. 10A-10F show human cadavers imaged with a contrast agent in accordance with embodiments of the present invention.
Figure 10B:
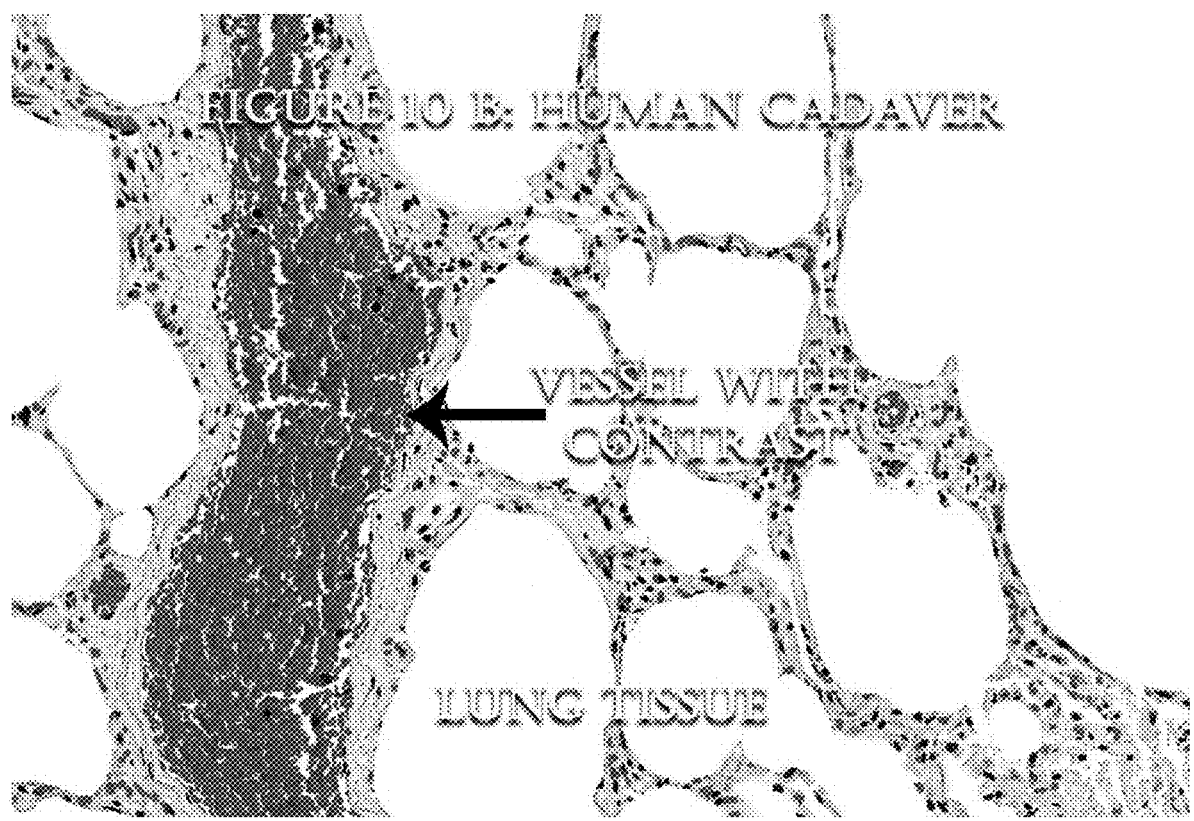
Figure 10C:
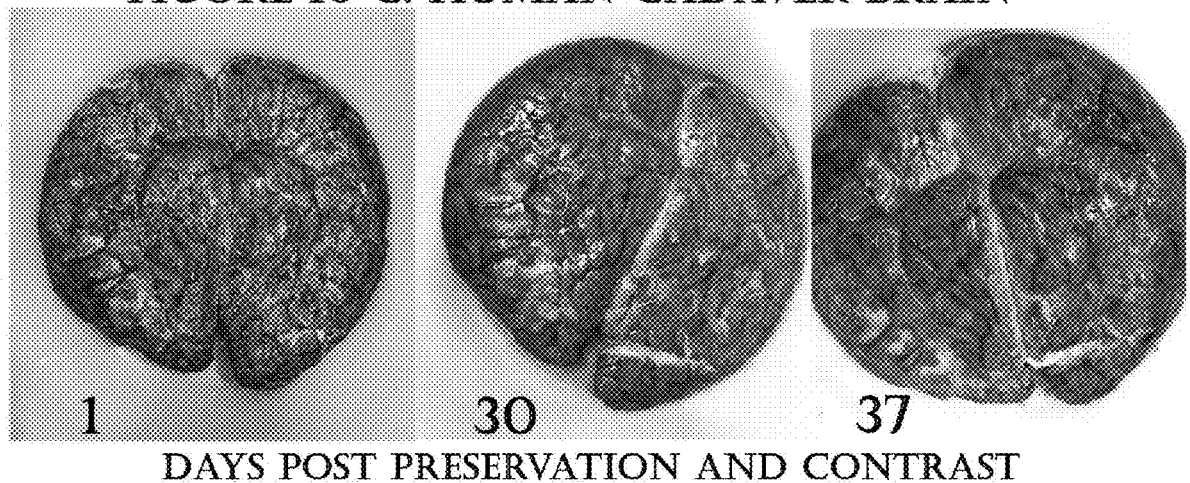

FIG. 10A shows muscle with an artery in the middle of the image well preserved histologically. The sample was taken 29 days post-preservation (37 days post-death), and placed in 10% formalin, which was the subject's first exposure to formalin. The amount of degradation observed was expected given that the cadaver was eight days post-mortem prior to preservation. However, further degradation was stopped using the inventive method. FIG. 10B shows lung tissue with a vessel filled with contrast agent. The sample collection times and storage were identical to that in FIG. 10A. Even though no formalin was used until 37 days post-death, the level of observed tissue preservation is excellent. FIG. 10C shows the excised brain of the cadaver at various time points. The brain was pulled from the cadaver 1-day post-preservation with contrast (9 days post-death) and stored uncovered in a refrigerator. The brain tissue was well formed, and retained color and shape over 37 days post-preservation and contrast with refrigeration only. Small white vessels can be seen representing the BRITEVU® contrast agent within the vasculature. Brain tissue normally begins to degrade within hours of removal from the brain case on fresh cadavers. This series demonstrates preservation of brain tissue without the use of formaldehyde, and no special care other than refrigeration.

Figure 10D:
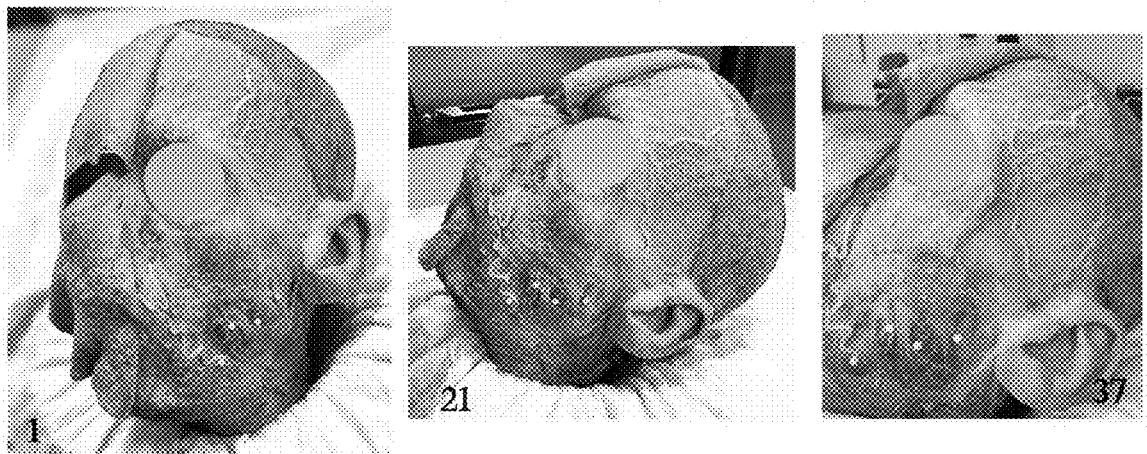

FIG. 10D shows a different cadaver head, not previously shown, at various timepoints after the inventive method was applied. While only the head was preserved and perfused with contrast agent using the inventive method, the procedure was similar to the other cadaver described in FIGS. 10A-10C, as the inventive method was applied eight days post-death. The far-right image shows the head at 37 days post-preservation and contrast, which is 45 days post-death. The vessels can be seen filled with the white BRITEVU® contrast agent. The cadaver's skin has been peeled away to reveal the underlying vessels, nerves, facia, and muscles. Small unlabeled pins have been placed for anatomy purposes. No additional preservatives were used after the initial inventive method described above.

Figure 10E:
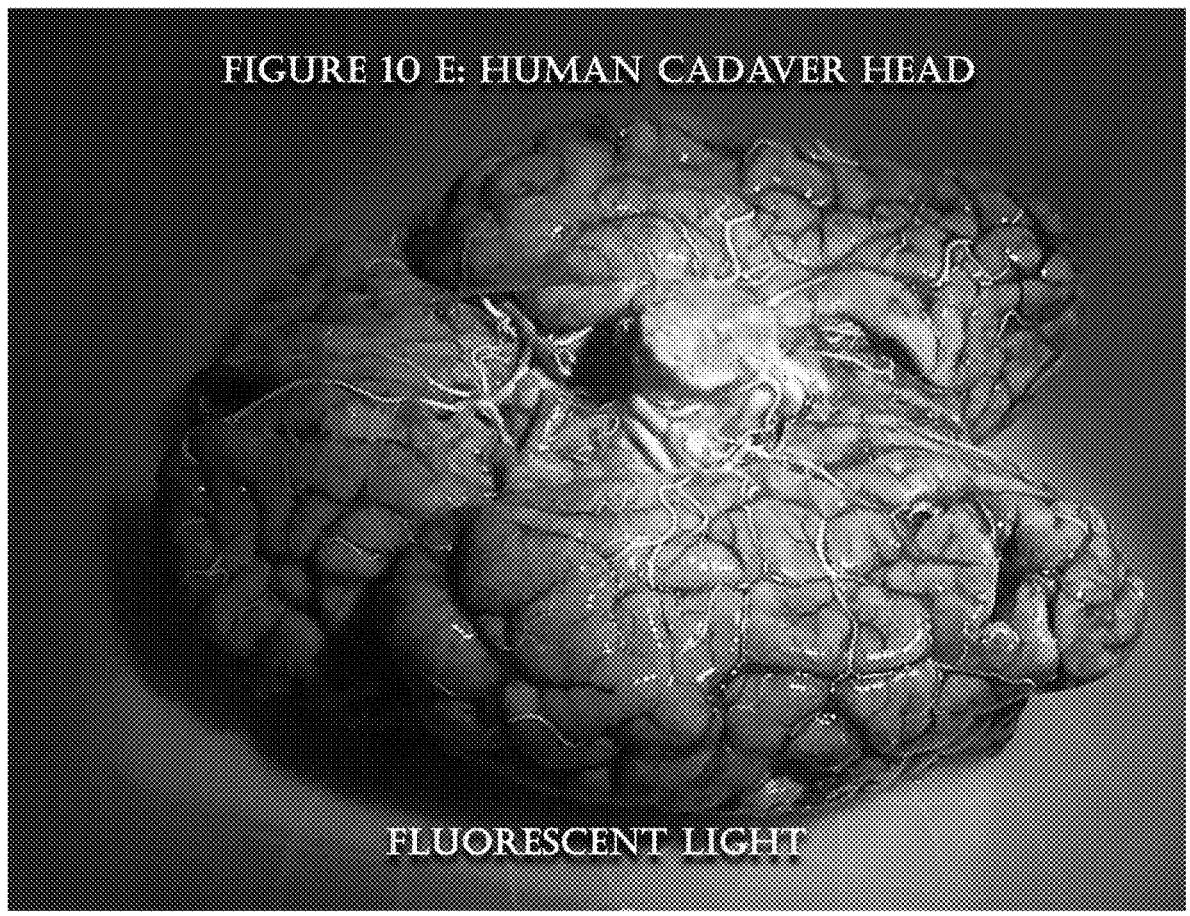
Figure 10F:
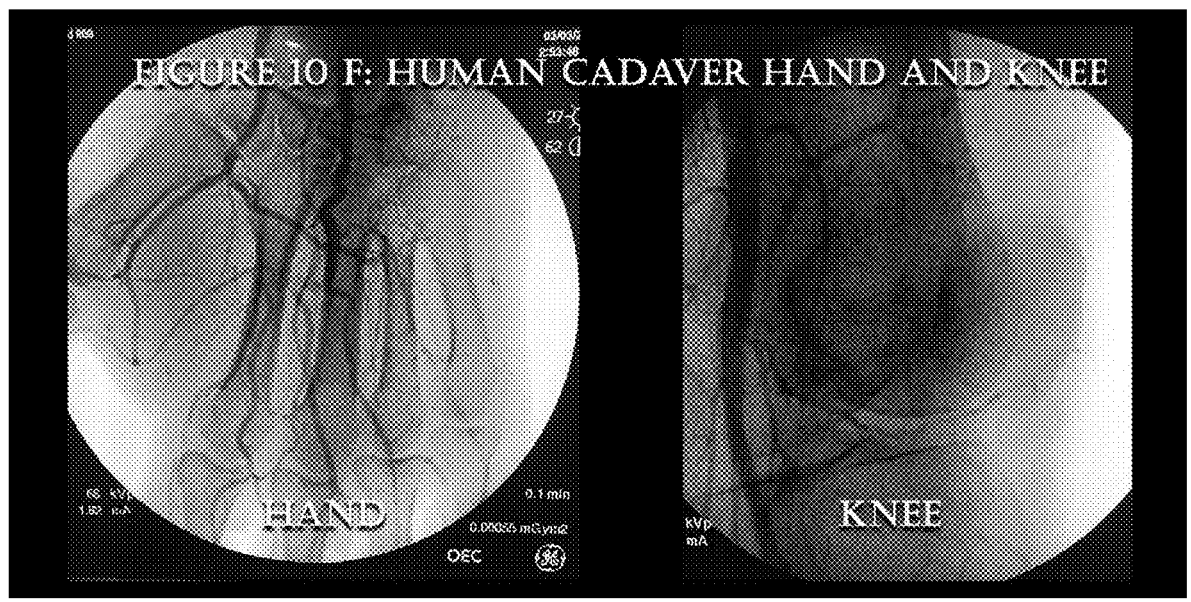

FIG. 10E shows the brain of a human cadaver removed from the brain case one day after being subjected to the inventive method, nine days post-death. In this image, a 395 nm black (fluorescent) light is used to light the brain. The fluorescein dye added to the contrast agent can be seen fluorescing in the blood vessels using the black light. FIG. 10F shows the hand (left image) and knee (right image) of a subject one day after being subjected to the inventive method, as viewed with a C-arm fluoroscopy unit. FIGS. 10E-10F demonstrate yet other ways of visualizing tissue using the inventive process.

In sum, the inventive method includes flushing a tissue of a subject with a solution, followed by preserving the tissue and introducing an imaging contrast agent into the tissue. Such method greatly improves the image quality of the vascular and skeletal system of an entire subject, such as an animal.

Any patents or publications mentioned in this specification are indicative of the level of those skilled in the art to which the invention pertains. These patents and publications are herein incorporated by reference to the same extent as if each individual publication was specifically and individually indicated to be incorporated by reference.

The foregoing description is illustrative of particular embodiments of the invention, but is not meant to be a limitation upon the practice thereof. The following claims, including all equivalents thereof, are intended to define the scope of the invention.

The invention claimed is:

1. A method comprising:
    flushing a subject with a first solution to substantially remove blood and blood components from the subject;
    preserving the subject, after said flushing, by introducing into the subject a non-formaldehyde-based preservation agent;
    flushing the subject with a second solution, after said preserving, to substantially remove said non-formaldehyde-based preservation agent; introducing, after said flushing the subject with the second solution, an imaging contrast agent into the subject; and
    internally imaging the subject.

2. The method of claim 1, further comprising introducing a second imaging contrast agent into the subject.

3. The method of claim 1, wherein at least one of the first solution and the second solution is hypotonic, isotonic, or hypertonic.

4. The method of claim 1, wherein at least one of the first solution and the second solution comprises an anticoagulant.

5. The method of claim 1, wherein preserving the subject comprises using an alcohol-based compound as a preservation agent.

6. The method of claim 1, wherein preserving the subject comprises using a salt compound as a preservation agent.

7. The method of claim 1, wherein the imaging contrast agent comprises an iodine-based agent, a silver-based agent, a barium-based agent, a microbubble-based agent, or an iron-based agent.

8. The method of claim 1, wherein the imaging contrast agent is radiodense.

9. The method of claim 1, wherein the imaging contrast agent is perfusible.

10. The method of claim 1, wherein the imaging contrast agent is diffusible.

11. The method of claim 1, wherein the imaging contrast agent is lanthanide-based.

12. The method of claim 1, further comprising:
    combining the imaging contrast agent with a carrier agent; and
    introducing the resulting combination into the subject.

13. A method comprising:
    flushing a subject with a hypotonic solution to substantially remove blood and blood components from the subject;
    introducing into the subject, after said flushing, a non-formaldehyde-based preservation agent;
    flushing the subject with a non-reactive fluid to substantially remove said non-formaldehyde-based preservation agent; introducing, after said flushing the subject with the non-reactive fluid,
    into the subject an imaging contrast agent; and
    internally imaging the subject.

14. The method of claim 13, wherein the internal imaging comprises CT, X-ray, ultrasound, MM, photography, or thermography.

15. The method of claim 13, wherein the imaging contrast agent is lanthanide-based.

16. The method of claim 1, wherein said second solution is a non-reactive fluid.

* * * * *